United States Patent [19]

Kozaki et al.

[11] Patent Number: 5,854,059
[45] Date of Patent: Dec. 29, 1998

[54] BIODEGRADATION OF AN ORGANIC COMPOUND AND PROCESS FOR UPGRADING THE ENVIRONMENT BY REMOVING THE AFORESAID COMPOUND

[75] Inventors: Shinya Kozaki, Sakurashin-machi; Tetsuya Yano; Chieko Mihara, both of Isehara; Takeshi Imamura, Chigasaki, all of Japan

[73] Assignee: Canon Kabushiki Kaisha, Tokyo, Japan

[21] Appl. No.: 835,741

[22] Filed: Apr. 10, 1997

[30] Foreign Application Priority Data

Apr. 11, 1996 [JP] Japan .................................. 8-089605

[51] Int. Cl.$^6$ .................................................. C12S 13/00
[52] U.S. Cl. ...................... 435/262; 435/262.5; 435/266; 435/244; 435/245
[58] Field of Search .................................. 435/189, 262.5, 435/262, 266, 244, 245, 248–250; 405/128; 166/246; 210/610, 611

[56] References Cited

U.S. PATENT DOCUMENTS

| 4,275,164 | 6/1981 | Masurekar | 435/227 |
|---|---|---|---|
| 4,877,736 | 10/1989 | Fliermans | 435/183 |

FOREIGN PATENT DOCUMENTS

| 0694611 | 1/1996 | European Pat. Off. . |
| 0730027 | 9/1996 | European Pat. Off. . |
| 2-92274 | 4/1990 | Japan . |
| 3-292970 | 12/1991 | Japan . |
| 6-70753 | 3/1994 | Japan . |
| 6-105691 | 4/1994 | Japan . |
| 6-227769 | 8/1994 | Japan . |
| WO89-09827 | 10/1989 | WIPO . |
| WO90-0690 | 6/1990 | WIPO . |
| WO92-17938 | 10/1992 | WIPO . |
| WO92-19738 | 11/1992 | WIPO . |

OTHER PUBLICATIONS

Hanson, et al., "Development of Methantrophs . . . Olefins", Preprint Preprint Extended Abstract, Div. Env. Chem. A.C.S., pp. 365–367, Sep. 1989.

Ewers, et al., "Selection of TCE . . . by TCE", Arch. Micro., 154, pp. 410–413 (1990).
Wackett, et al., "Survey of Microbial . . . Bacteria", Appl. and Envir. Micro., 55, 11, pp. 2960–2964 (1989).
Winter, "Efficient Degradation . . . *E. Coli*", Bio. Tech. 7, pp. 282–285, (1989).
Japan Sewage Works Assoc., 24, 273, pp. 27–33 (1987).
Negoro, et al., Growth of Microalgae . . . and No$_x$. 28/29, 1991, pp. 877–886, Appl. Biochem. & Biotech.
Beam, et al., "Microbial Degradation . . . Commensalism", J. Gen. Microb., (1974) 82, 163–169.
Embly, et al., "Lactobacillus . . . the Human Vagina", Int. J. System. Bacter. (1989) 39, 3, 368–370.
Nelson, et al., "Aerobic Metabolism . . . Isolate", Appl. & Environ. Microbiol. (1986) 52, 2, 383–83.
Nelson, et al., "Biodegradation of Trichloroethylene . . . Pathway", Appl. & Environ. Microbiol. (1987) 53, 5, 949–954.
Wackett, et al., "Degradation of Trichloroethylene . . . F1", Appl. & Environ. Microbiol. (1988) 54, 7, 1703–1708.
Tsien, et al., "Biodegradation of Trichloroethylene . . . OB3b", Appl. & Environ. Microbiol. (1989) 55, 12, 3155–1361.
Vannelli, et al., "Degradation of Halogenated . . . europaea", Appl. & Environ. Microbiol. (1990) 56, 4, 1169–1171.
Harker, et al., Trichloroethylene Degradation . . . JMP134, Appl. & Environ. Microbiol. (1990) 56, 4, 1179–1181.
Henry, et al., "Influence of Endogeneous . . . Aquifier", Appl. Environ. Microbiol. (1991) 57, 2, 236–244.
Shields, et al., "Selection of a Pseudomonas . . . Trichloroethylene", Appl. & Environ. Microbiol. 1992) 58, 12, 3977–3983.
Vandenbergh et al., "Metabolism . . . Pseudomonas Fluoresces", Appl. & Environ. Microbiol. (1988) 54, 9 pp. 2578–2579.

*Primary Examiner*—William H. Beisner
*Attorney, Agent, or Firm*—Fitzpatrick, Cella, Harper & Scinto

[57] ABSTRACT

An organic compound is biodegraded using JM1 (FERM BP-5352) by contacting the JM1 with an organic compound and culturing the JM1 in a medium including source of conjugated carbon which is citric acid, maleic acid or a salt thereof.

29 Claims, 29 Drawing Sheets

EXAMPLE 1

EFFECT OF ADDING SODIUM MALATE ON THE DEGRADATION OF PHENOL IN SOIL (30°C, SODIUM CITRATE 0.5%)

EXAMPLE 1

EFFECT OF ADDING SODIUM MALATE ON THE DEGRADATION OF PHENOL IN SOIL (30°C, SODIUM CITRATE 1%)

EXAMPLE 1

EFFECT OF ADDING SODIUM MALATE ON THE DEGRADATION OF PHENOL IN SOIL (30°C, SODIUM CITRATE 2.0%)

EXAMPLE 2

EFFECT OF ADDING SODIUM MALATE ON THE DEGRADATION OF PHENOL IN SOIL (30°C, SODIUM CITRATE 0.5%)

EXAMPLE 2

EFFECT OF ADDING SODIUM MALATE ON THE DEGRADATION OF PHENOL IN SOIL (15°C, SODIUM CITRATE 1.0%)

EXAMPLE 2

EFFECT OF ADDING SODIUM MALATE ON THE DEGRADATION OF PHENOL IN SOIL (15°C, SODIUM CITRATE 2.0%)

EXAMPLE 3

EFFECT OF ADDING SODIUM MALATE ON THE DEGRADATION OF PHENOL IN SOIL (10°C, SODIUM CITRATE 0.5%)

EXAMPLE 3

EFFECT OF ADDING SODIUM MALATE ON THE DEGRADATION OF PHENOL IN SOIL (10°C, SODIUM CITRATE 1.0%)

EXAMPLE 3

EFFECT OF ADDING SODIUM MALATE ON THE DEGRADATION OF PHENOL IN SOIL (10°C, SODIUM CITRATE 2.0%)

EXAMPLE 10

EFFECT OF ADDING SODIUM MALATE ON THE DEGRADATION OF PHENOL IN SOIL (15°C, SODIUM CITRATE 2.0%)

EXAMPLE 5

EFFECT OF ADDING SODIUM MALATE ON THE DEGRADATION OF TCE IN SOIL (30°C, SODIUM CITRATE 0.5%)

EXAMPLE 5

EFFECT OF ADDING SODIUM MALATE ON THE DEGRADATION OF TCE IN SOIL (30°C, SODIUM CITRATE 1.0%)

EXAMPLE 5

EFFECT OF ADDING SODIUM MALATE ON THE DEGRADATION OF TCE IN SOIL (30°C, SODIUM CITRATE 2.0%)

EXAMPLE 6

EFFECT OF ADDING SODIUM MALATE ON THE DEGRADATION OF TCE IN SOIL (15°C, SODIUM CITRATE 0.5%)

EXAMPLE 6

EFFECT OF ADDING SODIUM MALATE ON THE DEGRADATION OF TCE IN SOIL (15°C, SODIUM CITRATE 1.0%)

EXAMPLE 6

EFFECT OF ADDING SODIUM MALATE ON THE DEGRADATION OF TCE IN SOIL (15°C, SODIUM CITRATE 2.0%)

EXAMPLE 7

EFFECT OF ADDING SODIUM MALATE ON THE DEGRADATION OF TCE IN SOIL (10°C, SODIUM CITRATE 0.5%)

EXAMPLE 7

EFFECT OF ADDING SODIUM MALATE ON THE DEGRADATION OF TCE IN SOIL (10°C, SODIUM CITRATE 1.0%)

EXAMPLE 7

EFFECT OF ADDING SODIUM MALATE ON THE DEGRADATION OF TCE IN SOIL (10°C, SODIUM CITRATE 2.0%)

EXAMPLE 8

EFFECT OF ADDING SODIUM MALATE ON THE DEGRADATION OF TCE IN SOIL (15°C, SODIUM CITRATE 2.0%)

EXAMPLE 9

EFFECT OF ADDING SODIUM MALATE ON THE DEGRADATION OF CIS-1,2-DCE IN SOIL (15°C, SODIUM CITRATE 2.0%)

EXAMPLE 9

EFFECT OF ADDING SODIUM MALATE ON THE DEGRADATION OF TRANS-1, 2-DCE IN SOIL (15°C, SODIUM CITRATE 2.0%)

EXAMPLE 9

EFFECT OF ADDING SODIUM MALATE ON THE DEGRADATION OF 1,1-DCE IN SOIL (15°C, SODIUM CITRATE 2.0%)

EXAMPLE 10

EFFECT OF ADDING SODIUM MALATE ON THE TCE DEGRADATION IN POLLUTED WATER (30°C, SODIUM CITRATE 2.0%)

EXAMPLE 11

EFFECT OF ADDING SODIUM MALATE ON THE TCE DEGRADATION IN POLLUTED WATER (15°C, SODIUM CITRATE 2.0%)

EXAMPLE 12

EFFECT OF ADDING SODIUM MALATE ON THE TCE DEGRADATION IN POLLUTED WATER (10°C, SODIUM CITRATE 2.0%)

EXAMPLE 13

EFFECT OF ADDING SODIUM MALATE ON THE TCE DEGRADATION IN SOIL
BY CONTINUOUS GAS PERMEABILITY (30°C, SODIUM CITRATE 2.0%)

EXAMPLE 14

EFFECT OF ADDING SODIUM MALATE ON THE TCE DEGRADATION IN SOIL
BY CONTINUOUS GAS PERMEABILITY (15°C, SODIUM CITRATE 2.0%)

EXAMPLE 15

EFFECT OF ADDING SODIUM MALATE ON THE TCE DEGRADATION IN SOIL BY CONTINUOUS GAS PERMEABILITY (10°C, SODIUM CITRATE 2.0%)

BIODEGRADATION OF AN ORGANIC COMPOUND AND PROCESS FOR UPGRADING THE ENVIRONMENT BY REMOVING THE AFORESAID COMPOUND

FIELD OF THE INVENTION

The present invention relates to a process for the biodegradation of an organic compound by means of a microorganism, and also to a process for upgrading the environment by biodegradation of a pollutant.

RELATED BACKGROUND ART

Pollution of the environment by chlorinated organic compounds which are harmful to living organisms and difficult to degrade has recently become a serious problem. In particular soil in places where high technology manufacturing has been carried out, for example integrated circuit factories in Japan and other countries, has been found to be contaminated by chlorinated aliphatic hydrocarbon compounds, for example tetrachloroethylene (PCE), trichloroethylene (TCE), dichloroethylene (DCE) and the like. A number of environmental surveys have been carried out in which such chlorinated aliphatic hydrocarbon compounds have been detected. It has been postulated that residual chlorinated organic compounds in soil are carried via rainwater to the groundwater where they can become spread over a wide area. These compounds are strongly suspected to be carcinogenic, and also they are stable under environmental conditions so that contamination of ground water which can be used as a source of drinking water is a serious problem to society.

It is therefore an important problem from the standpoint of protection of the environment to be able to purify groundwater and other aqueous media, soil, and the gas phase surrounding them by removal or degradation of chlorinated organic compounds. There is also a requirement for techniques to be developed which enable this purification to be carried out.

For example, it has been proposed to use an adsorption treatment using active carbon, or a degradation treatment by means of light or heat. However, these approaches may not be practical from the standpoints of cost and operational complexity.

On the other hand, it has recently been proposed to biodegrade chlorinated organic compounds which are environmentally stable (e.g. chlorinated aliphatic hydrocarbon compounds such as TCE or the like) by means of a microorganism. Various studies have been initiated in order to put the process to practical use. The advantage of degrading chlorinated organic compounds into harmless substances using a microorganism is that there is no requirement for any special chemicals, and labour and maintenance costs can be avoided.

The following are examples of microbial strains which can degrade TCE:

Welchia alkenophila sero 5 (U.S. Pat. No. 4,877,736, ATCC 53570),
Welchia alkenophila sero 33 (U.S. Pat. No. 4,877,736, ATCC 53571),
Methylocystis sp. strain M (Agric. Biol. Chem., 53, 2903 (1989), Biosci. Biotech. Biochem., 56, 486 (1992)),
*Methylosinus trichosorium* OB3d (Am. Chem. Soc. Natl. Meet. Dev. Environ. Microbiol., 29, 365 (1989), Appl. Environ. Microbiol., 55, 3155 (1989), Appl. Biochem. Biotechnol., 28, 877 (1991), Japanese Laid-Open Patent Application (JPUA) 02-092274, JPUPA 03-292970),
Methylomonas sp. MM2 (Appl. Environ. Microbiol., 57, 236 (1991)),
*Alcaligenes denitrificans* ssp. xylosoxidans JE75 (Arch. microbiol., 154, 410 (1990)),
*Alcaligenes eutrophus* JM134 (Appl. Environ. Microbiol., 56, 1179 (1990)),
*Mycobacterium vaccae* JOB5 (J. Gen. Microbiol., 82, 163 (1974), Appl. Environ. Microbio., 54, 2960 (1989), ATCC 29678),
*Pseudomonas putida* BH (Journal of Japan Sewage Work Association, 24, 27 (1987)),
Pseudomonas sp. strain G4 (Appl. Environ. Microbiol., 52, 383 (1986), ibid. 53, 949 (1987), ibid. 54, 1951 (1989), ibid. 56, 1279 (1990), ibid. 57, 1935 (1991), U.S. Pat. No. 4,925,802, ATCC 53617). This strain was originally classified as *Pseudomonas cepacia* then classified as Psudomonas sp.
*Pseudomonas mendocina* KR-1 (BiolTechnol., 7, 282 (1989)),
*Pseudomonas putida* F1 (Appl. Environ. Microbiol., 54, 1703 (1988), ibid., 54, 2578 (1988)),
*Pseudoinonas fluorescens* PFL12 (Appl. Environ. Microbiol., 54, 2578 (1988)),
*Pseudomonas putida* KWI-9 (JPUA 06-070753),
*Pseudomonas cepacia* KK01 (JPUPA 06-227769),
*Nitrosomnonas europaea* (Appl. Eviron. Microbiol. 56, 1159 (1990) ), *Lactobacillus vaginalis* sp. nov. (Int. J. Syst. Bacteriol., 39, 368 (1989), ATCC 49540) and so on.

All the above strains, however, require chemical substances such as aromatic compounds and methane as an inducer in order to express their TCE degrading activity. For example, when the above microorganisms are used for degrading TCE, aromatic compounds such as phenol and toluene are very effective as an inducer. However, these compounds are also harmful to the environment, and therefore if they are released into the environment, complicated procedures and monitoring are required. Methane can also act as an effective inducer, but it is dangerous and difficult to introduce it into and control it within an environment because it is a flammable gas. Because of the harmful or dangerous substances needed to induce the activity of these strains, purification processes using them are difficult to apply to the practical upgrading of the environment.

In order to mitigate the above problems, Nelson et al developed a process for degrading chlorinated organic compounds using tryptophan which is an amino acid as an inducer (Japanese Laid-Open Patent Application 04-502277). However, tryptophan resembles other strains in that it requires an inducer. As a TCE degrading enzyme is an induced enzyme, the activity of a TCE degrading enzyme expressed by means of an inducer is normally maintained only for a period of several hours, after which a further addition of inducer is required. Furthermore, TCE degradation gives rise to competitive inhibition based on the existence of the inducer, and the efficiency of the TCE degradation process is significantly reduced. Therefore the fundamental problem still remains. Furthermore, in the Nelson et al process release of the inducer into the environment is possible, but there is still a need for a purification process which is simple, effective and of low cost.

Attempts have been made to introduce into a host bacterium a plasmid containing a DNA fragment encoding oxygenase or hydroxylase, a TCE degrading enzyme or the like so that the modified bacterium will subsequently express a TCE degrading activity by means of a harmless inducer or without any inducer at all. Bacterial strains from which the DNA fragment originates include:

*Pseudomonas mendocina* KR-1 (Japanese Laid-Open Patent Application 02-503866),

*Pseudomonas putida* KWI-9 (Japanese Laid-Open Patent Application 06-105691),

*Pseudomonas putida* BH (Proceedings of the 3rd Meeting of Assembly for study of groundwater/soil contamination and of countermeasures against it, p.213 (1994)).

However, various problems arise in the use of recombinant DNA technology. For example, very expensive substances may be needed as an inducer, for example IPTG (isopropylthiogalactopyranoside) which is a very expensive material. The stability of the plasmid in the host strain may be insufficient, with a result that the growth or activity of the microorganism may be insufficiently stable. Furthermore, the release of recombinant strains of microorganisms into the environment will inevitably be restricted by the need to obtain regulatory approval. Seales et al have reported a further attempt to solve the problem using Pseudomonas sp. strain G4 whose TCE degradation characteristic has been induced by mutagenization using a transposon rather than an inducer, for example toluene, phenol or the like (Appl. Environ. Microbiol., 58, p.3977 (1992), WO92/19738). A mutant derived from strain G4, however, does not have a sufficient TCE degradation activity, and its stability is questionable because of the transposon. Furthermore, the transposon itself contains a resistant gene providing aminoglucoside resistance, which may give rise to the problem that other microorganisms may be undesirably affected through horizontal transfer when the genetically engineered organism is released into the environment.

SUMMARY OF THE INVENTION

It is an object of the invention to provide a process for biodegrading an organic compound effectively and stably.

A further object of the present invention is to provide a process by which a polluted environment can be effectively and stably upgraded.

According to a first aspect of the invention there is provided a process for biodegrading an organic compound using the microorganism JM1 (FERM BP-5352). Said process may involve the steps of contacting the strain JM1 with the organic compound, and cultivating the strain JM1 in a culture medium which includes a source of conjugated carbon which may be citric acid or its salts and malic acid or its salt.

According to a further aspect of the invention there is provided a process for upgrading an environment by removal of a pollutant present in the environment using strain JM1 (FERM BP-5352). The process may comprise the steps of contacting the microorganism strain JM1 with the organic compound present in the environment, and cultivating the JM1 in a culture medium which includes a source of conjugated carbon, typically citric acid and its salts, and malic acid and its salts.

The present applicants have selected a particular organism which can degrade organic compounds without the need for an inducer and exhibits excellent degradation characteristics. The organism was deposited on Dec. 22,1995 in the National Institute of Bioscience and Human Technology, Agency of Industrial Science and Technology, Tsukuba city, Ibaraki prefecture, Japan under the Budapest Treaty (International Deposit Accession No. FERM BP-5352, Identification Reference Corynebacterium sp. JM1). Hereinafter the novel strain will be referred to as "strain JM1". This strain was at first thought to belong to the genus Corynebacterium, but it has been found that this is not the case, and therefore the identification reference for the FERM BP-5352 strain has been renamed as strain JM1.

In general, when a microorganism is used for environmental purification treatment, it is important to make the strain exhibit its degradation characteristics stably and effectively in a number of different circumstances. In particular, when a microorganism is used to upgrade waste fluid or soil including TCE, the microorganism should preferably exhibit a high and stable degradation activity even under severe conditions of temperature, environment, pH, oxygen concentration, other constituents and the like. The present inventors have studied the strain JM1 with the objective of finding suitable constituents of a culture medium which can enable the strain JM1 to exhibit its high degradation activity under some or all of the severe conditions mentioned above. The present inventors have found that a source of conjugated carbon which may be selected from citric acid and its salts and malic acid and its salts is very suitable as a constituent of culture medium.

BRIEF DESCRIPTION OF THE DRAWINGS

The accompanying figures show pollutant degradation in accordance with the examples listed below at the sodium citrate concentration listed, and at the temperature listed.

| FIG. NO. | EXAMPLE NO. | SODIUM CITRATE CONCENTRATION (%) | TEMPERATURE (°C.) |
|---|---|---|---|
| 1 | 1 | 0.5 | 30 |
| 2 | 1 | 1 | 30 |
| 3 | 1 | 2 | 30 |
| 4 | 2 | 0.5 | 15 |
| 5 | 2 | 1 | 15 |
| 6 | 2 | 2 | 15 |
| 7 | 3 | 0.5 | 10 |
| 8 | 3 | 1 | 10 |
| 9 | 3 | 2 | 10 |
| 10 | 4 | 2 | 15 |
| 11 | 5 | 0.5 | 30 |
| 12 | 5 | 1 | 30 |
| 13 | 5 | 2 | 30 |
| 14 | 6 | 0.5 | 15 |
| 15 | 6 | 1 | 15 |
| 16 | 6 | 2 | 15 |
| 17 | 7 | 0.5 | 10 |
| 18 | 7 | 1 | 10 |
| 19 | 7 | 2 | 10 |
| 20 | 8 | 2 | 15 |
| 21 | 9 | 2 | 15 |
| 22 | 9 | 2 | 15 |
| 23 | 9 | 2 | 15 |
| 24 | 10 | 2 | 30 |
| 25 | 11 | 2 | 15 |
| 26 | 12 | 2 | 10 |
| 27 | 13 | 2 | 30 |
| 28 | 14 | 2 | 15 |
| 29 | 15 | 2 | 10 |

DETAILED DESCRIPTION OF THE INVENTION

Figure 1:
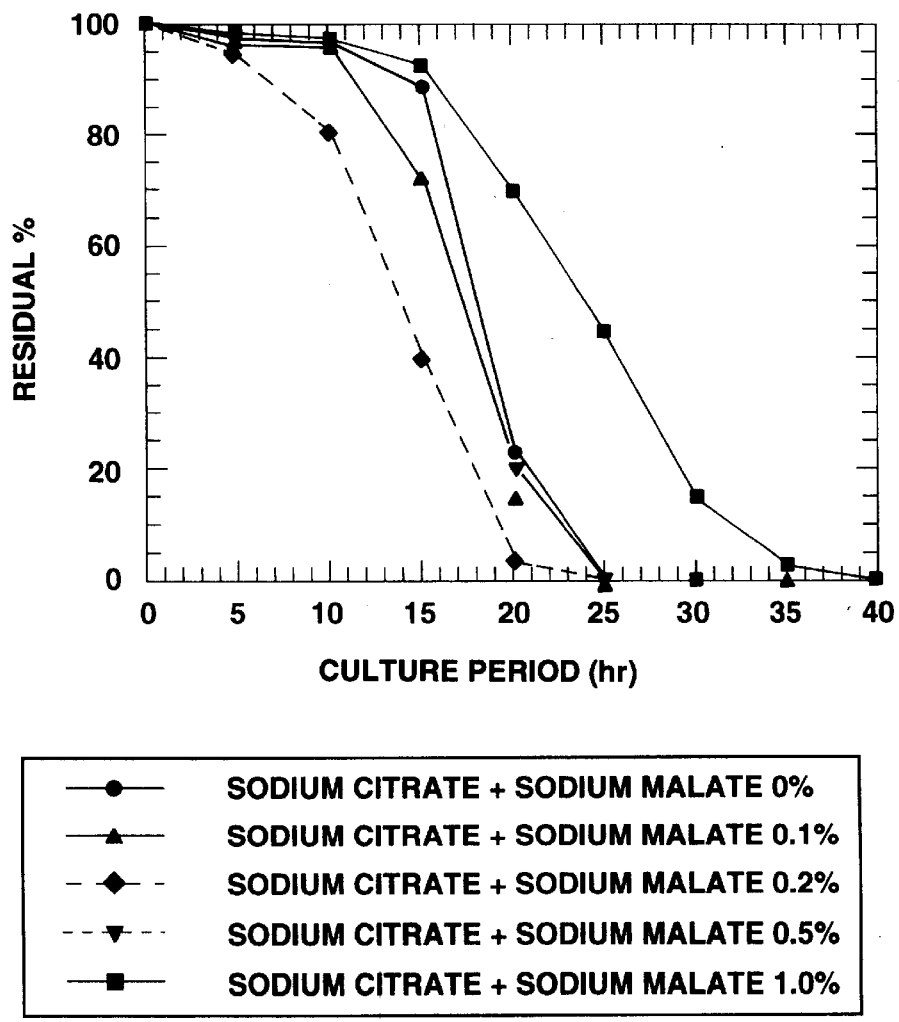
In FIGS. 1–10, the pollutant is phenol, in FIGS. 11–20 and 24–29 it is TCE, and in FIGS. 21, 22 and 23 it is cis-1,2-DCE, trans-1,2-DCE and 1,1-DCE.

The microorganism used in the present process for biodegrading an organic compound or upgrading an environment is a mutant strain of a particular microorganism (International Deposit under the Budapest Treaty, Accession No. FERM BP-5102) which can degrade aromatic compounds and chlorinated aliphatic hydrocarbon compounds in the presence of an inducer. The mutant strain has been deposited as FERM BP-5352/Identification Reference strain JM1 under the Budapest Treaty. The bacteriological characteristics of the strain JM1 are as follows:

| Gram staining and morphology | Gram-negative rod |
|---|---|
| Growth condition in each medium | |
| BHIA | good |
| MacConkey | possible |
| Colour of colony | cream |
| Optimum growth temperature | 25° C. > 30° C. > 35° C. |
| Motility | negative (in semisolid medium) |
| TSI (slant/butt) | alkali/alkali $H_2S(-)$ |
| Oxidase | positive (weak) |
| Catalase | positive |
| Fermentation of sugars | |
| glucose | negative |
| sucrose | negative |
| raffinose | negative |
| maltose | negative |
| urease | positive |
| Esculin hydrolysis (B-glucosidase) | positive |
| Nitrate reduction | negative |
| Indole productivity | negative |
| Glucose aciditication | negative |
| Arginine dihydrase | negative |
| Gelatin hydrosis (protease) | negative |
| B-galactosidanse | negative |
| Assimilation of each compound | |
| glucose | negative |
| L-arabinose | negative |
| D-mannose | negative |
| D-mannitol | negative |
| N-acetyl-D-glucosamine | negative |
| maltose | negative |
| potassium gluconate | negative |
| n-capric acid | positive |
| adipic acid | negative |
| dl-maltic acid | positive |
| sodium citrate | positive |
| phenyl acetate | negative |

When organic materials and pollutants are biodegraded by the above mentioned JM1 strain, the culture medium should include a source of conjugated carbon which may be citric acid or its salts and malic acid or its salts. When the above mentioned strain is cultivated in a culture medium containing the above mentioned conjugated carbon source, it can biodegrade organic compounds and pollutants stably and effectively under severe conditions, for example at temperatures as low as 10° C. or less.

Citric acid salts and malic acid salts are commercially available, for example as sodium salts and the potassium salts.

Cultivation of the JM1 strain in a culture medium including the above mentioned conjugated carbon source may be carried out before the JM1 strain is contacted with the organic compound. Alternatively, the strain JM1 may be cultivated in a culture medium in which the organic compounds and pollutants are present. In the latter case, an increase of the amount of the strain JM1 microorganisms in the culture medium, and a decrease of the chemical compounds as a result of degradation by the strain JM1 can occur simultaneously.

In the above mentioned embodiment, an ordinary culture medium which contains essential nutrients for strain JM1 and citric acid and its salts and malic acid or its salts can be used as the basic culture medium. For example M9 medium which contains a variety of minerals supplemented with a source of conjugated carbons is available. Where there is used a soil or an aqueous medium containing the essential minerals for the growth of the strain JM1, it is unnecessary to add further minerals.

The composition of the M9 medium in 1 liter; pH 7.0 is as follows:

$Na_2HPO_4$:6.2g $KH_2PO_4$:3.0g

NaCl:0.5g $NH_4Cl$:1.0g

The following are examples of inorganic materials which may be added to the M9 medium:

nitrilotriacetic acid:1.5

$MgSO_4$:3.0

$MnSO_4$:0.5

NaCl:1.0

$FeSO_4$:0.1

$CaCl_2$:0.1

$ZnSO_4$:0.1

$CuSO_4$:0.1

$AlK(SO_4)_2$:0.1

$H_3BO_3$:0.1

$NaMoO_4$:0.1

$NiCl_2$:0.1 g/l (in 1 liter; 600ul)

The concentration of citric acid, malic acid or salts thereof can be varied depending upon the organic materials to be degraded. A concentration of citric acid or citrate of 0.5–2.0% in the culture medium is preferred, particularly 2.0% sodium citrate. A concentration of malic acid or salt thereof of 0.01–1% in the culture medium is preferred, especially 0.1–0.5%. Sodium malate 0.2% is very preferable, if mixed with sodium citrate because the degradation activity of the strain JM1 for organic compounds has been found to be significantly increased.

The strain JM1 can be cultured under aerobic conditions and both liquid culture and solid culture can be used. The range of culture temperatures can be 7.5°–35° C., preferably 15°–30° C. Before strain JM1 is cultivated in the culture medium, a precultivation can be carried out to increase the amount of JM1 strain available. In that case malate acid or its salt, particularly for example 1–2% sodium malate may be incorporated into the culture medium as a source of carbon.

The degradation of organic compounds by means of the strain JM1, in accordance with this embodiment may be carried out by contacting the strain JM1 with the organic compounds to be degraded in a culture medium including the source of conjugated carbon and in the presence of the organic compounds. In the process of upgrading the environment using the strain JM1, the activated strain JM1 can be contacted with pollutants in the polluted environment, for example an aqueous medium, soil, gas phase or the like.

The organic compounds which may be degraded using the strain JM1 may include for example aromatic compounds (phenol, toluene, cresol, etc) and chlorinated aliphatic hydrocarbon compounds (trichloroethylene, dichloroethylene, etc). Any method may be used for contacting the strain JM1 with the targeted compounds, as long as the conditions do not interfere with the degradation activity of the strain JM1. The batch method, semi-continuous method and continuous method may be used. The microorganism can be used in a semi-immobilized state or in a state where it is immobilized on a suitable solid carrier. The targets to be treated may include waste fluid, soil, and gas phase media, and the method of treatment carried out will depend on local needs.

In the present invention, the degradation treatment of pollutants in aqueous media can be carried out by contacting the microorganism with the pollutant. A number of main uses are shown below, but the present invention is not intended to be limited to them. The present invention is applicable to any purification treatment for polluted aqueous media.

The easiest and simplest process is for the microorganism to be introduced directly into a polluted liquid solvent. In that case, it is desirable to adjust the pH value, salt concentration, temperature, pollutant concentration etc of the aqueous medium, but the degradation activity of the microorganism is maintained unless the aqueous medium is extremely acid, alkali or of high salt concentration.

Another possibility is to cultivate the strain JM1 in a culture vessel including a source of conjugated carbon compound provided in advance, and then to introduce the microorganism into the polluted aqueous medium in a vessel at a given flow rate so as to carry out the degradation treatment. The introduction and discharge of the aqueous medium may be carried out continuously or intermittently depending upon the degradation capacity available. Batch methods may also be used. Preferably a control system is used to optimise the concentration of pollutant to give the best results.

In a further process, the strain JM1 is adhered to a carrier such as soil particles, and the carrier is introduced into a reaction vessel after which the polluted aqueous medium is introduced into the vessel and the degradation treatment is carried out. In this case, the JM1 strain to be adhered to the carrier can be cultivated in a culture medium in advance, or it can be cultivated in a carrier in which the source of conjugated carbon is present. In the latter case, cultivation of the JM1 strain and degradation of pollutants can be carried out at the same time.

In addition to soil particles any other suitable carrier can be used. However, it is desirable to select a carrier having a good retention of microorganisms and a stable gas permeability. For example, various microorganism carriers which have been used generally in bioreactors in the drug manufacturing industry, the food industry, liquid waste treatment systems and the like can be used because they provide suitable habitats for microorganisms. In particular, inorganic particulate carriers such as porous glass, ceramics, metal oxides, activated charcoal, kaolinite, bentonite, zeolite, silica gel, alumina, anthracite, and so on can be used. Gel carriers can be used such as starch, agar, chitin, chitosan, polyvinyl alcohol, alginic acid, polyacrylamide, carrageenan, agarose, gelatin, and so on can be used. Cellulosic ion-exchange materials can be used as can other ion-exchange resins. Cellulose derivatives, glutaric aldehyde, polyacrylic acid, polyurethane and polyester may also be used. Natural materials can be used for example cotton, hemp, paper, etc. which are cellulosic, also sawdust, wood powder, bark and other lignin-containing materials can also be used.

In a further form of the invention, degradation of soil pollutants can be carried out by contacting the JM1 strain with the soil pollutants. The main uses are shown below but are not intended to limit the present invention. The present strain is applicable to a wide variety of purification treatments for polluted soil.

The easiest and simplest process is to introduce the JM1 strain directly into polluted soil. In this case, the JM1 strain may be cultivated in advance in a culture medium, or it may be introduced direct into the soil together with the source of conjugated carbon. Introduction of the strain JM1 or the strain JM1 together with the culture medium may be carried out by spraying it onto the surface of the soil, and when the treatment is extended deep underground, by introducing it through a well opening underground. Application of air pressure, water etc. allows the microorganism to become spread over a wide area of the soil and increases the effectiveness of the process. In this case, it is desirable to adjust various properties of the soil so that they are suitable for the microorganisms used in this process. The growth of the microorganism is speeded up in the presence of carriers such as soil particles and it is therefore desirable that the process is carried out in soil.

A further process involves adhering the strain JM1 to a carrier, after which the carrier is charged into a reaction vessel and then the contents of the reaction vessel are introduced into the primary aquifer of the polluted soil to carry out the degradation treatment. The reaction vessel may be formed by a wall or a film surrounding a wide area of the soil. The carrier may be as mentioned above. The JM1 strain to be adhered to the carrier can be cultivated in advance in a culture medium, or it can be cultivated on the carrier together with the source of conjugated carbon. In the latter case, cultivation of the strain JM1 and degradation of the pollutant occurs at the same time.

In a yet further form of the present process, degradation treatment for gas phase pollutants can be carried out by contacting the strain JM1 with gaseous pollutants. The main uses are indicated below, but the invention is not limited to these uses, and a wide variety of polluted gas phases can be treated according to the invention.

In one process, for example, the JM1 strain is cultivated in the culture vessel in advance, after which a contaminated gas is introduced into the vessel at a suitable flow rate and undergoes degradation treatment. A wide variety of methods of introducing the gas can be used, but desirably the introduction of the gas also brings about agitation of the culture medium and promotes its aeration. Introduction and discharge of the gas may be continuous or intermittent depending upon the degradation capacity of the medium in the vessel. Preferably a control system is provided responsive to the concentration of pollutant to give optimum results.

A further possibility is to adhere the microorganism to soil particles or other carriers which are introduced into the reaction vessel, after which the polluted gas to undergo degradation treatment is introduced into the vessel. The carriers may be as mentioned above. The JM1 strain adhered to the carriers can be cultivated beforehand in a culture medium or can be cultivated in a carrier together with the source of conjugated carbon. In the latter case cultivation of the JM1 strain and degradation of the pollutant occur at the same time. In the purification of contaminated gas, the strain can be introduced before or after the carrier material is added to the culture medium. To improve the efficiency of the degradation reaction, it is preferable to maintain the carbon source, water content, oxygen concentration etc. at optimum levels.

The ratio of carrier to water in a reaction vessel can be determined depending on the growth of the microorganism and the gas permeability of the medium. The shape of the vessel can be selected depending upon the amount and concentration of the gas to be treated, but preferably it is designed so that the contact of gas with the microorganism held on the carrier can be enhanced. The vessel may take the form of a column, tube, tank or box, and a vessel of any of these forms can be connected to an exhaust dust and a filter to form a single unit. A polluted gas can be absorbed by the carrier material at the beginning of the reaction, and there are relatively few cases where the effect of using the microorganisms is not exhibited. After a certain amount of the material has been degraded on the surface of the carrier material, further pollutant can be absorbed by the surface of the material. Thus the degradation restores the absorption power of the material, and the capacity of removing contaminants is not saturated so that a certain amount of degradation activity is maintained.

Embodiments of the above process can be used to upgrade the environment and to treat a wide variety of liquid waste, soil and to treat the air, whether in an open system or in a closed system. The microorganism can be used in a variety of states, including immobilisation on a carrier, and a variety of methods for speeding up the growth of the microorganism can be used. The invention can be used to biodegrade organic compounds efficiently and stably at temperatures of 10° or less (low temperature conditions).

The invention is further illustrated in the following examples:

EXAMPLE 1

Figure 2:
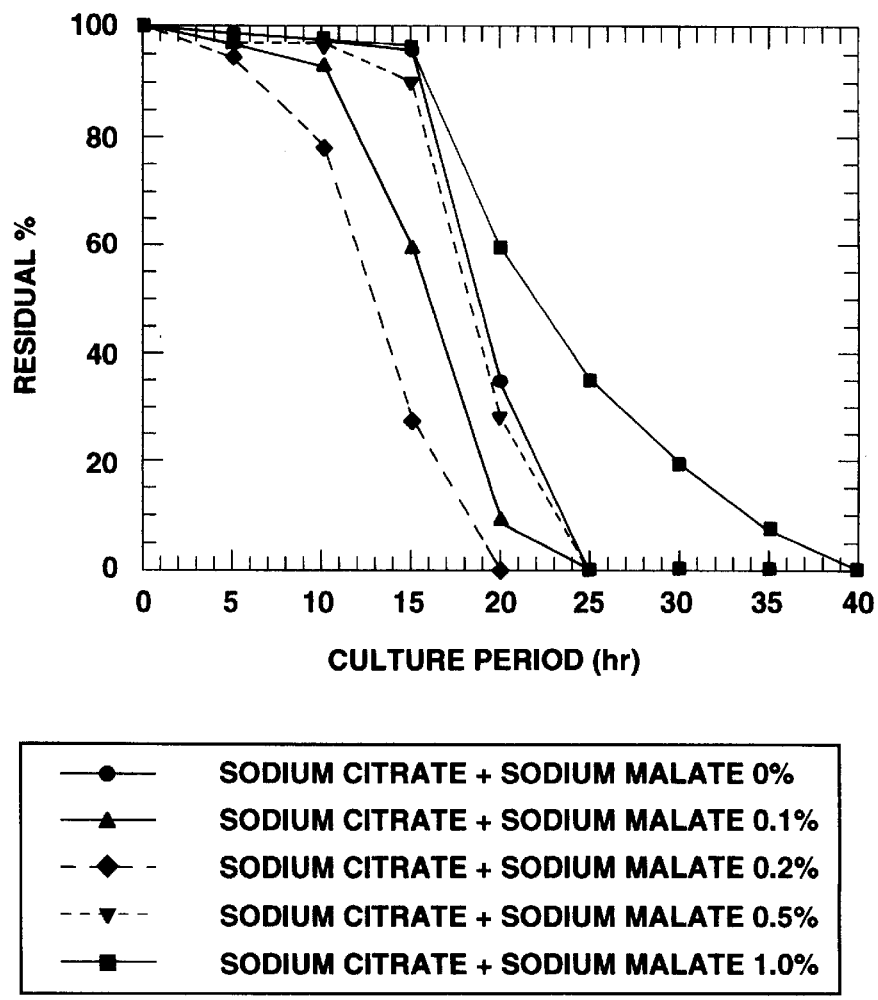
Figure 3:
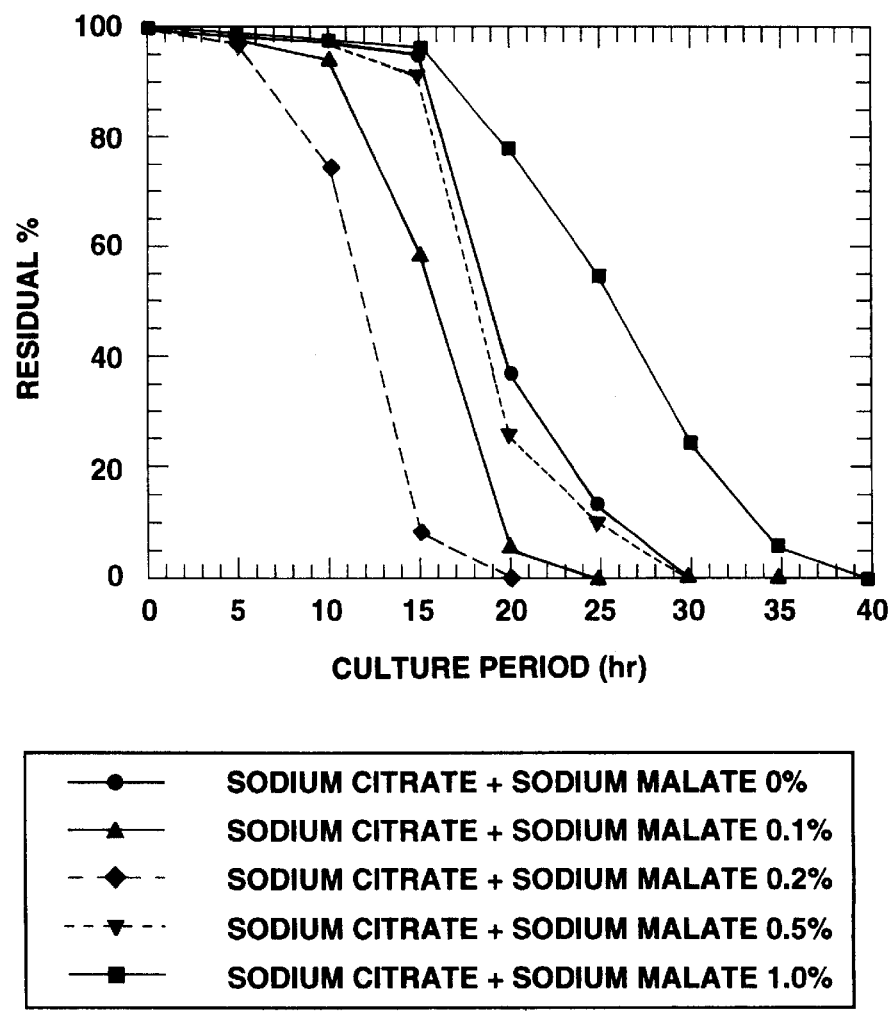

Degradation of phenol using the strain JM1 at 30° C. in a sand system using various nutrition conditions A comparison was made of the degradation activity in a system using a 67.5 ml vial containing 60 g of screened sand obtained from Sawara in Japan. As a preliminary step, an M9 culture medium including 2.0% of sodium malate and minerals was inoculated with strain JM1 (FERM BR-5352) after which the strain was cultivated for three days at 15° C. with shaking. Six samples of the M9 culture medium (6ml) which included 0.5% of sodium citrate and respectively 0%, 0.1%, 0.2%, 0.5%, 1% and 2% concentration of sodium malate were prepared. Each sample of the M9 culture medium was inoculated with 60 μl (1/100 volume) of pre-cultivated strain JM1, and phenol was added as the material to be degraded so as to produce a final concentration of phenol of 300 ppm. A plurality of the 67.5% ml vials containing 60 g of Sawara sand was prepared and the above mentioned samples of M9 culture medium were added into them. Each vial was corked with a silicone rubber cap and cultivated at 30° C. without shaking. The phenol concentration in each bottle was measured continually by means of a spectrophotometer. The above mentioned experiment was repeated and the phenol concentration was measured as described above, except that M9 culture medium containing 1% and 2% concentrations of sodium citrate were used. The result of these experiments is shown in FIGS. 1, 2 and 3 which show the effect of adding sodium malate at various concentrations of sodium citrate.

EXAMPLE 2

Figure 4:
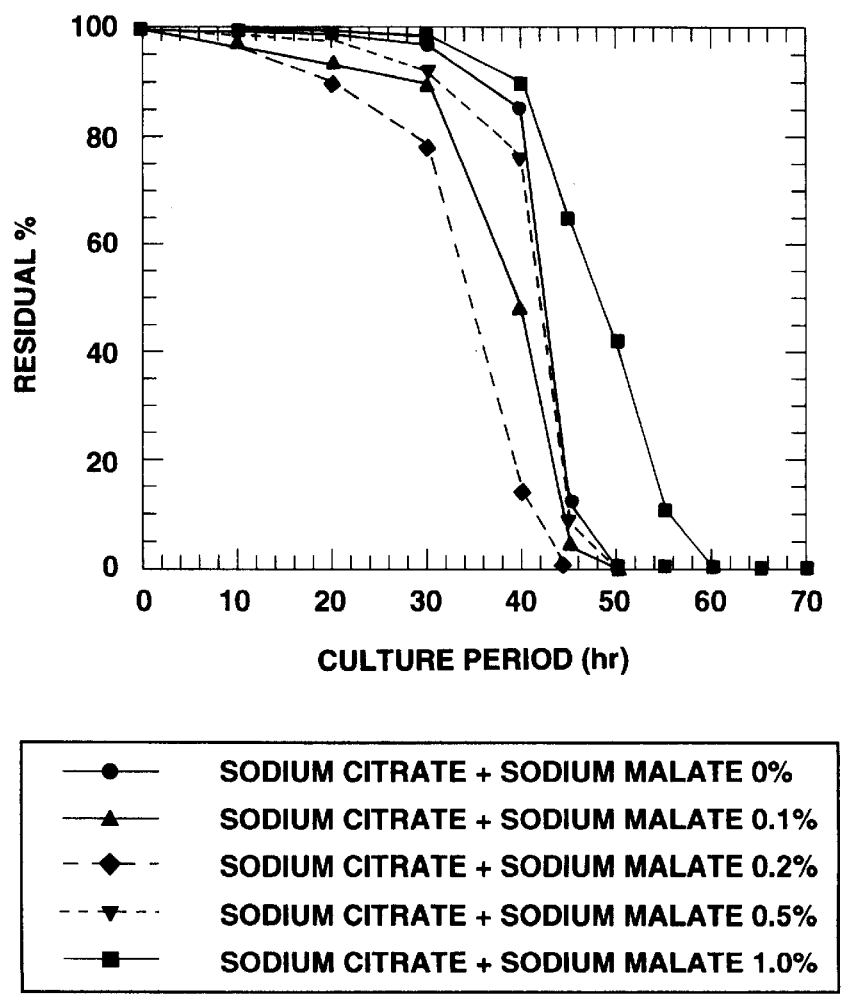
Figure 5:
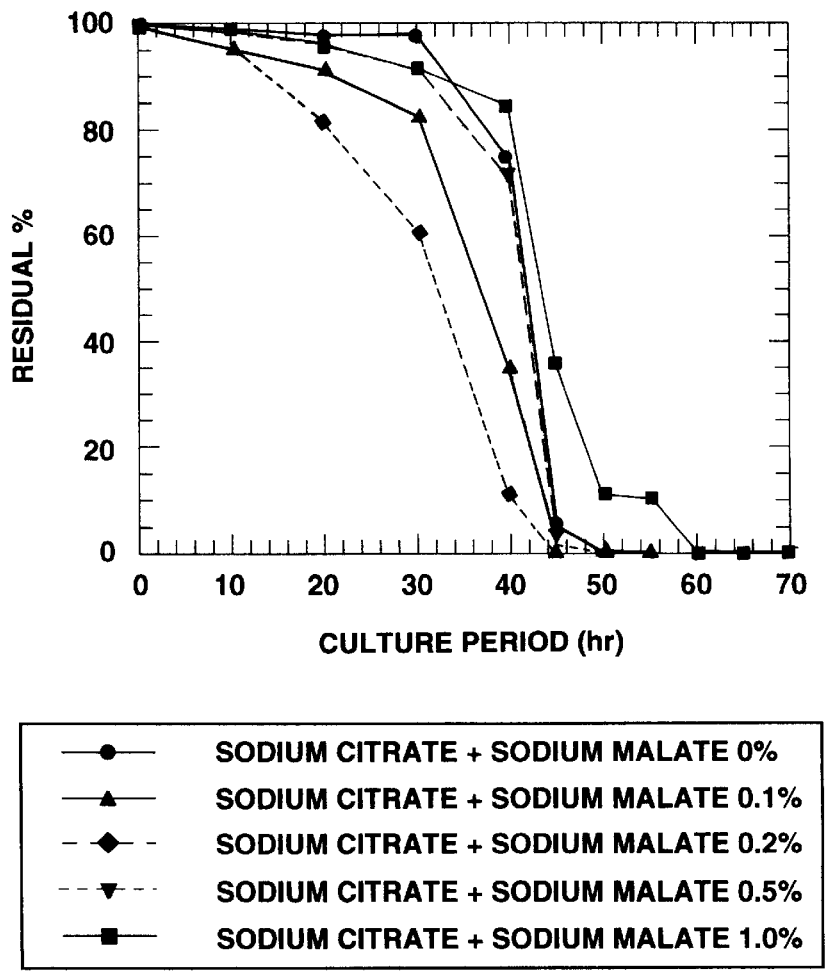
Figure 6:
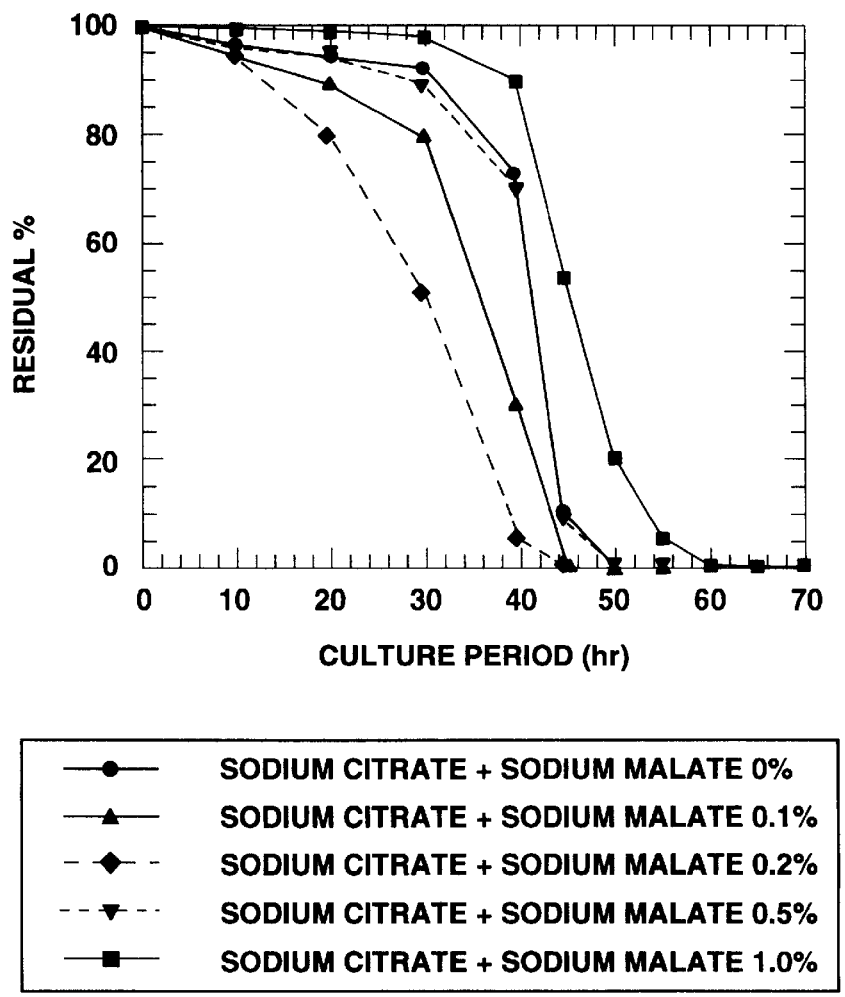

Degradation of phenol using strain JM1 at 15° C., sand system using various nutrients The phenol degradation efficiency was measured as in Example 1 except that each sample of M9 culture medium in each vial was cultivated without shaking at 15° C. The results are shown in FIGS. 4–6.

EXAMPLE 3

Figure 7:
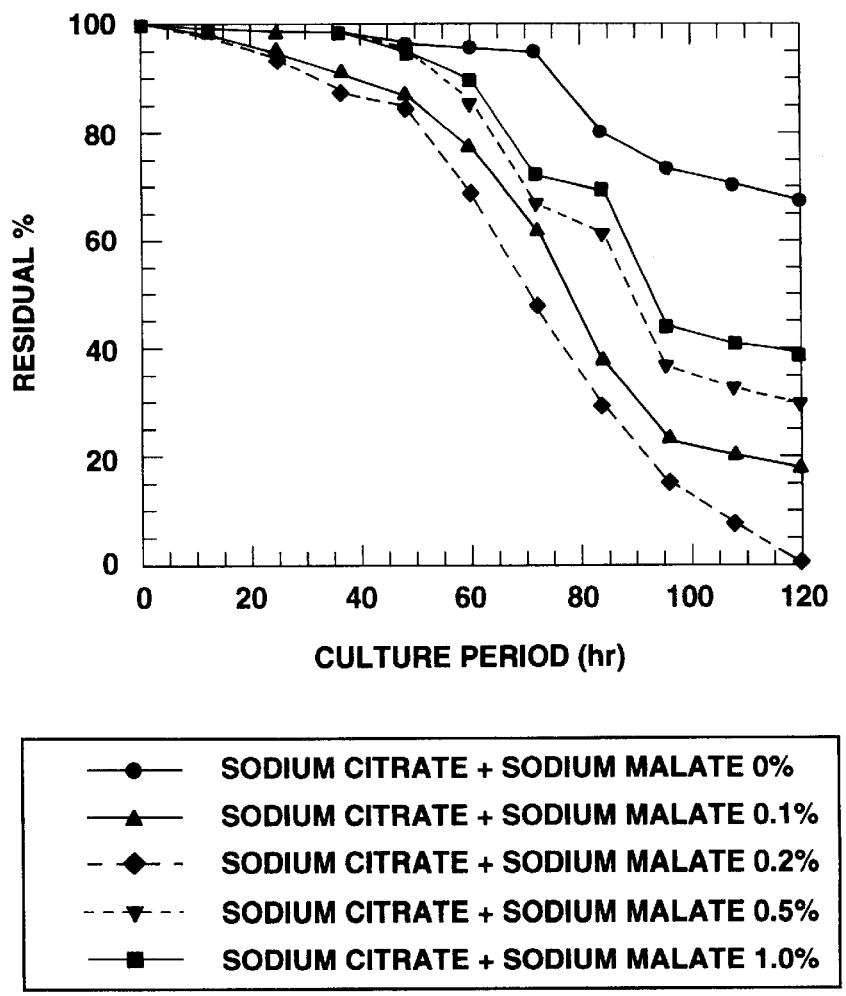
Figure 8:
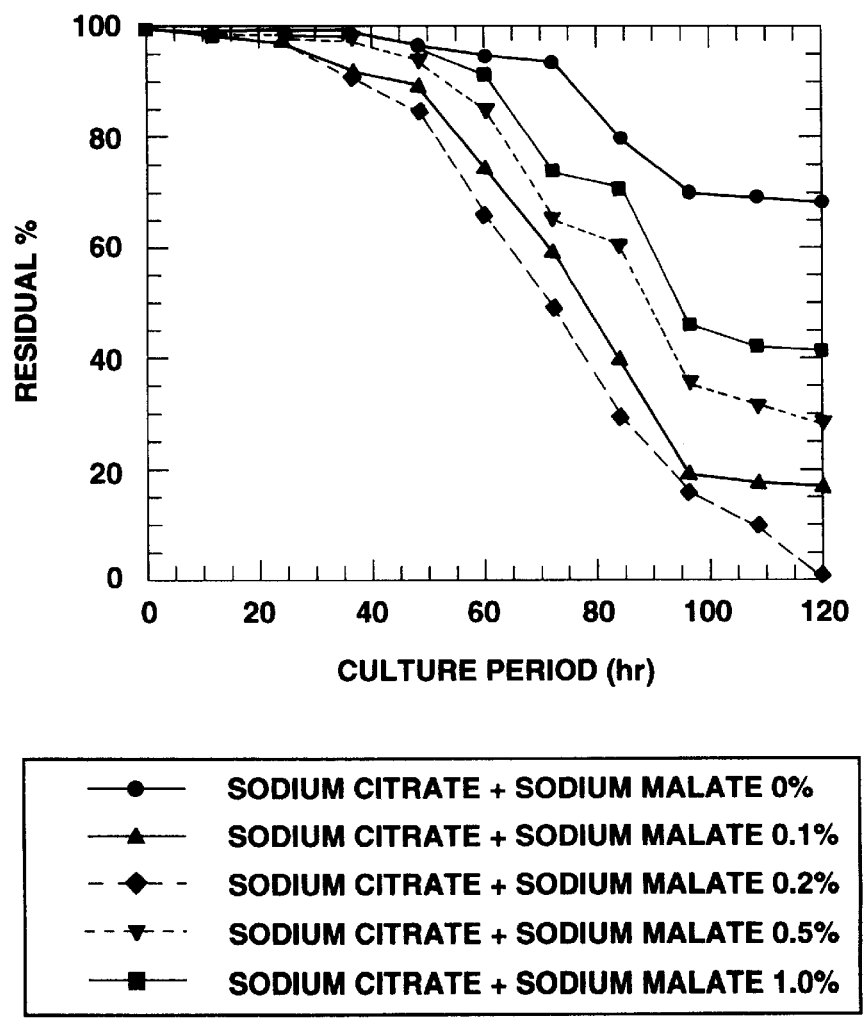
Figure 9:
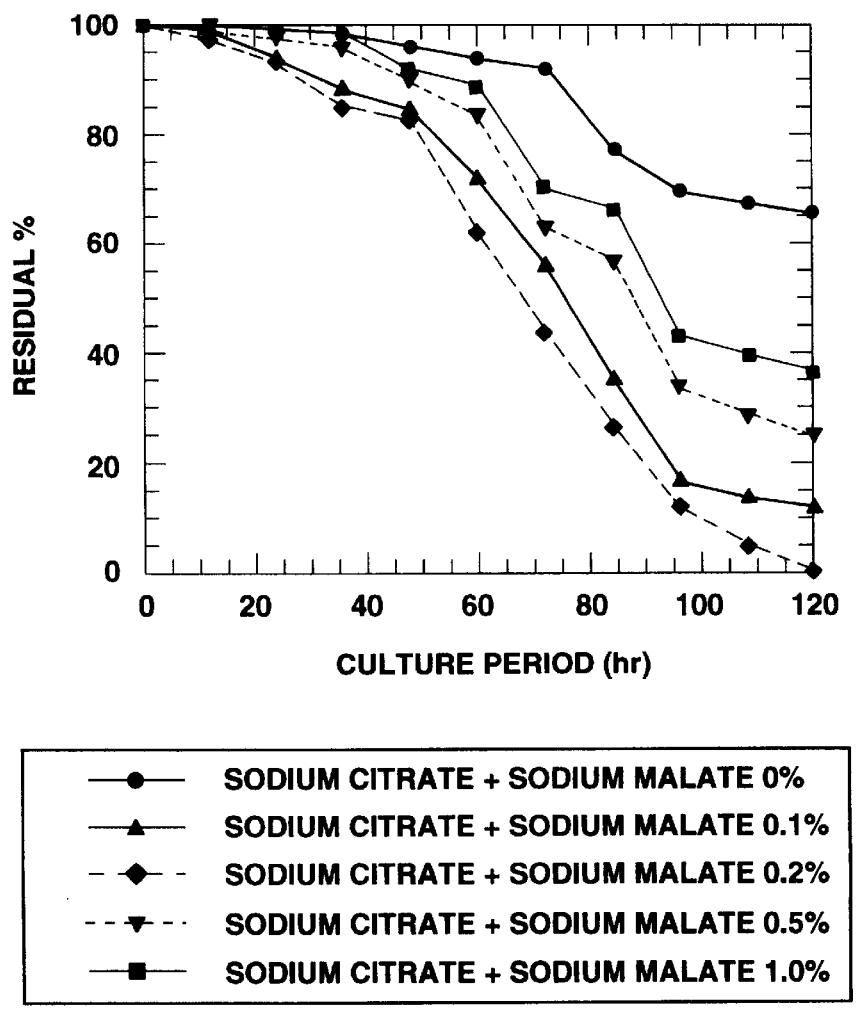

Degradation of phenol using JM1 strain 10° C., sand system using various nutrients The phenol degradation efficiency was measured in the same way as in Example 1 except that each sample of the M9 culture medium in each vial was cultivated statically at 10° C. The results are shown in FIGS. 7–9.

EXAMPLE 4

Figure 10:
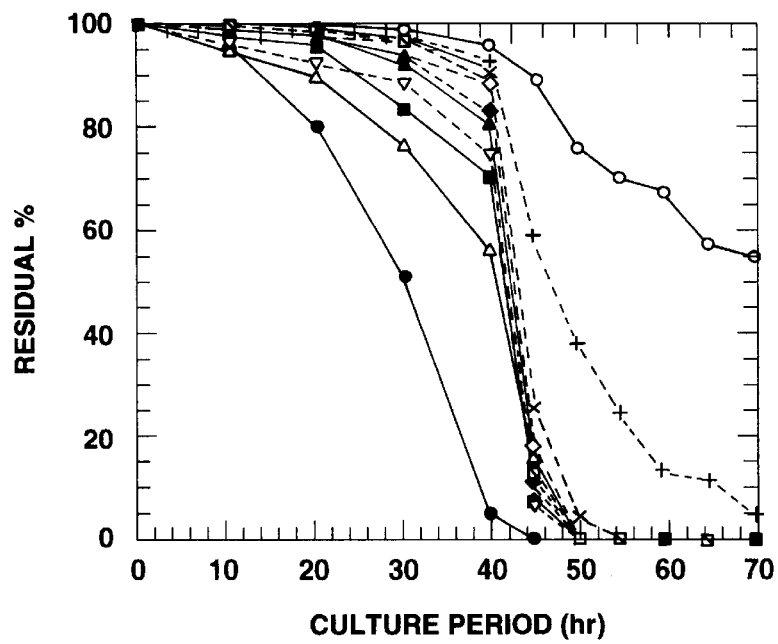
Figure 10:
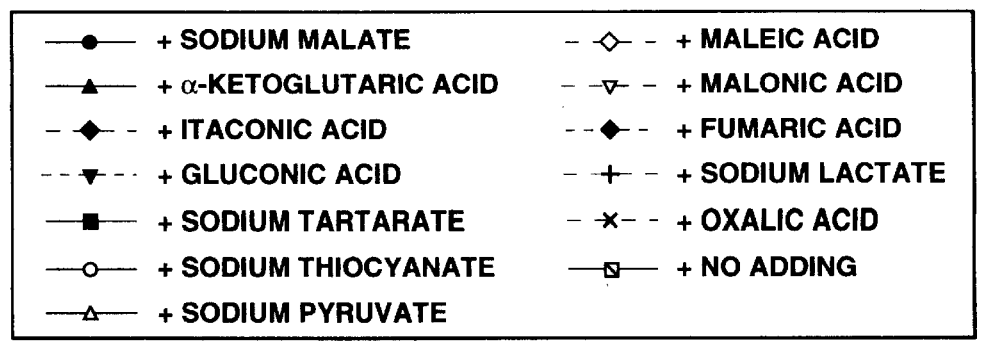

Degradation of phenol using strain JM1 (15° C., sand system) using various nutrients Comparison of the degradation activity of the microorganism in a 67.5ml volume vial containing 60 grams of Sawara sand was carried out. First the JM1 strain was pre-cultivated as described in Example 1. Then twelve samples of M9 culture medium (6ml) including 2% sodium citrate and 2% sodium citrate plus 2% concentration of various organic acids or salts. The organic acids or salts used were sodium malate, alpha-ketoglutaric acid, itaconic acid, gluconic acid, tartaric acid, sodium thiocyanate, sodium pyruvate, maleic acid, malonic acid, fumaric acid, sodium lactate and oxalic acid. Each sample of M9 culture medium was inoculated with 60 μl (1/100 volume) of pre-cultivated JM1, and phenol was added as the material to be degraded so as to provide a 300 ppm final concentration of phenol. A plurality of 67.5 ml vials was prepared to which were added 60 grams of Sawara sand followed by the above mentioned samples of M9 culture medium. Each vial was sealed with a silicone stopper and cultivated at 15° C. without shaking. The phenol concentration was measured continuously by a spectrophotometer. The result of this experiment was shown in FIG. 10.

EXAMPLE 5

Degradation of TCE using strain JM1 (3° C., sand system)

Figure 11:
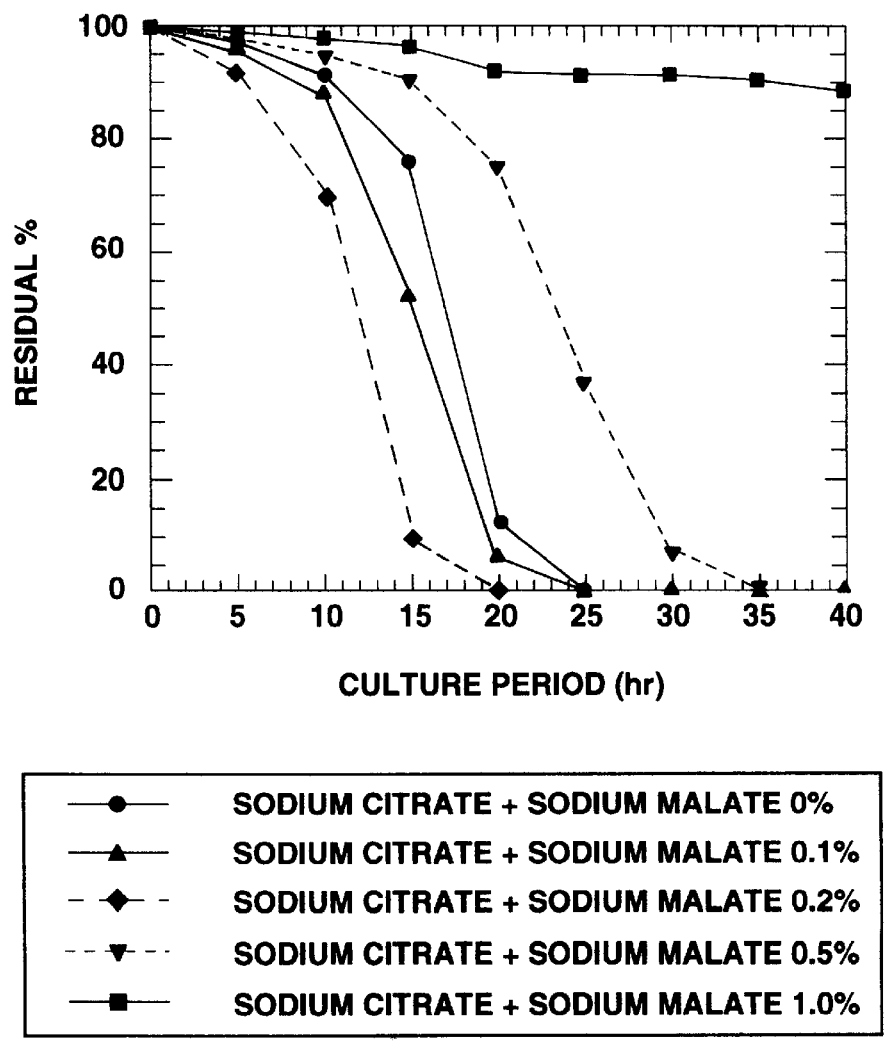
Figure 12:
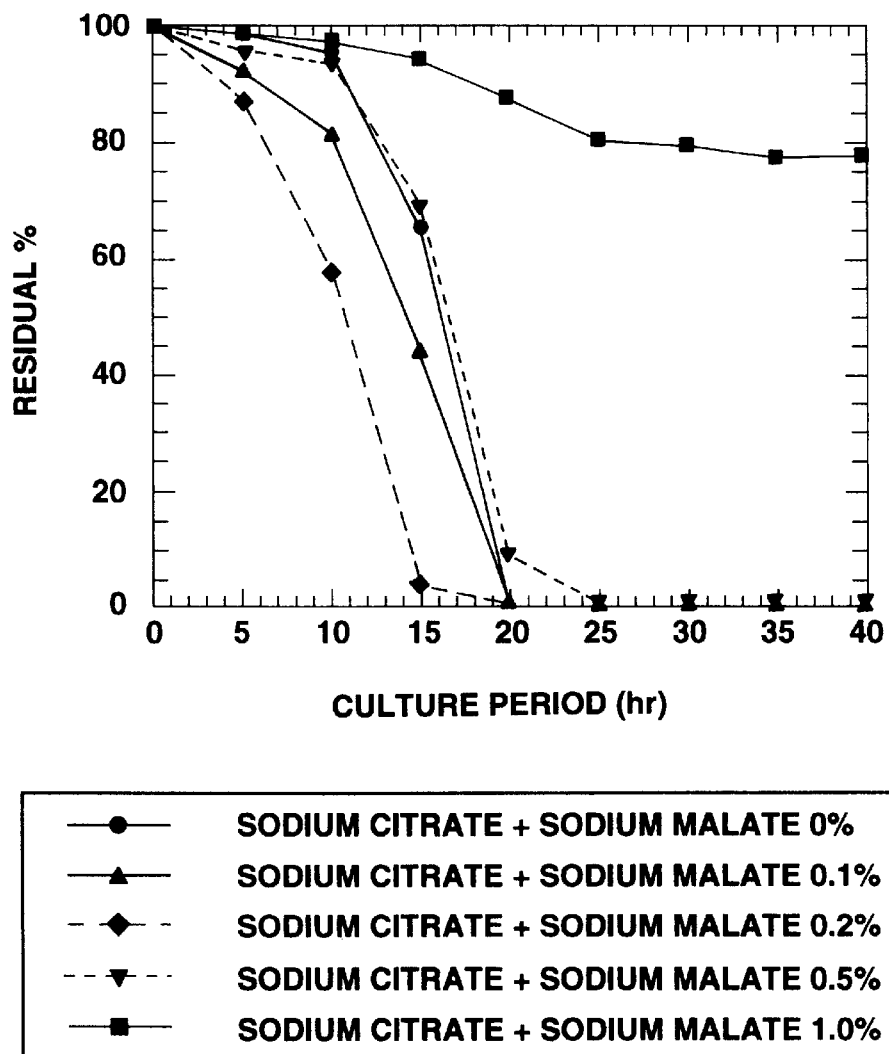
Figure 13:
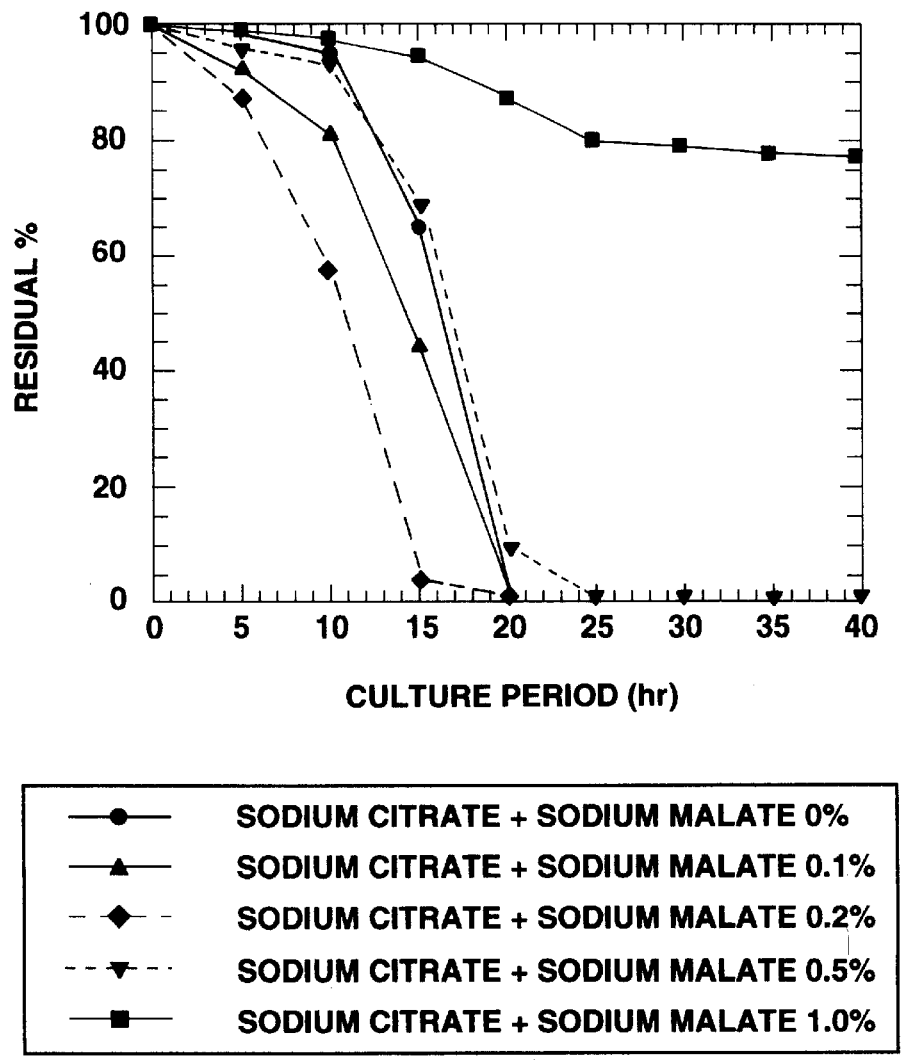

Degradation measurements were made using 67.5 ml vials containing 60 g of Sawara sand. The strain JM1 was pre-cultivated in M9 culture medium as disclosed in Example 1. Then six samples of the M9 culture medium (6ml) which included 0.5% of sodium citrate and respectively 0%, 0.1%, 0.2%, 0.5%, 1% and 2% concentrations of sodium malate were prepared. Each sample of M9 culture medium was inoculated with 60ml (1/100 volume) of the pre-cultivated strain JM1. Then a plurality of the 67.5ml vials containing 60 g of Sawara sand were prepared and samples of the M9 culture medium were added into each vial. Each vial was closed by a butyl rubber stopper, and an aluminium stopper. In these bottles, air including TCE was introduced so that the final concentration of TCE was 10 ppm. Then these. M9 culture media were cultivated at 30° C. without shaking and the degradation of TCE was continually measured. The residual TCE was measured in the headspace using gas chromatography (FID detector). In a reference experiment, the same system was used, but the strain JM1 was not added and the quantity of TCE was measured in the same way. Residues of TCE for the various experiments are shown in FIGS. 11–13.

EXAMPLE 6

Figure 14:
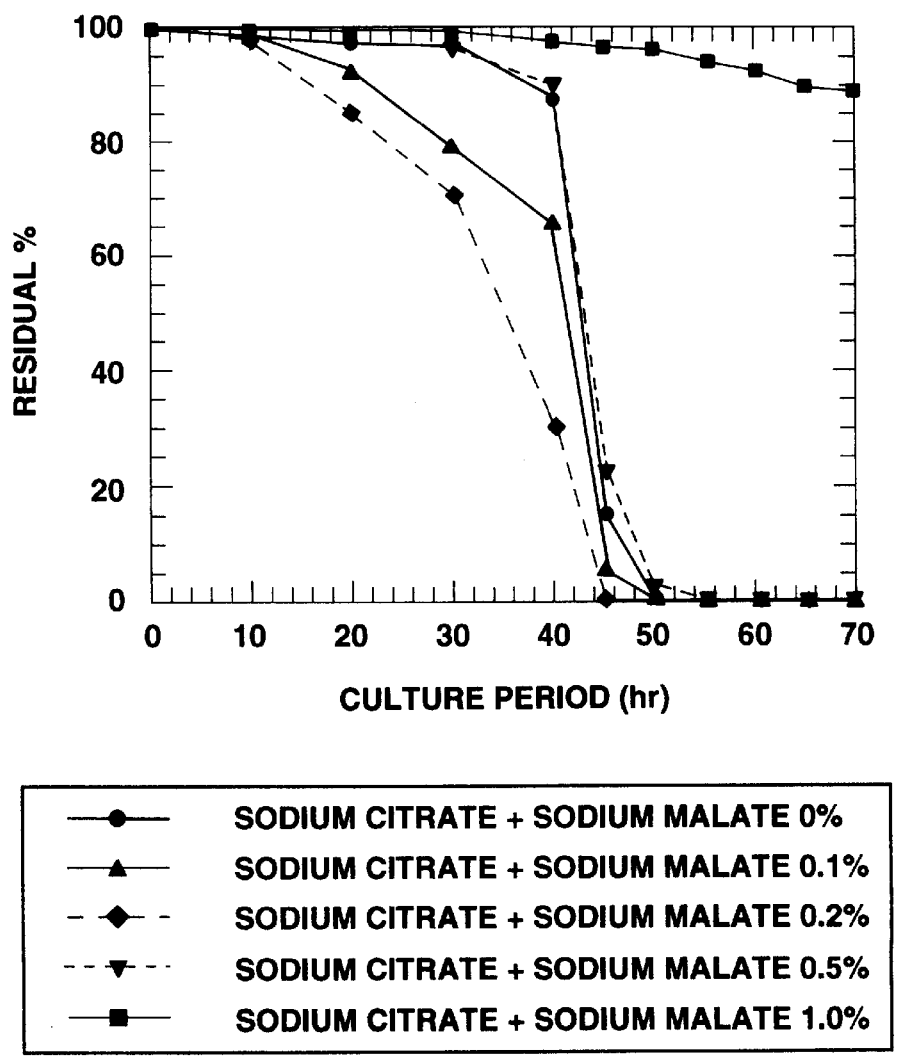
Figure 15:
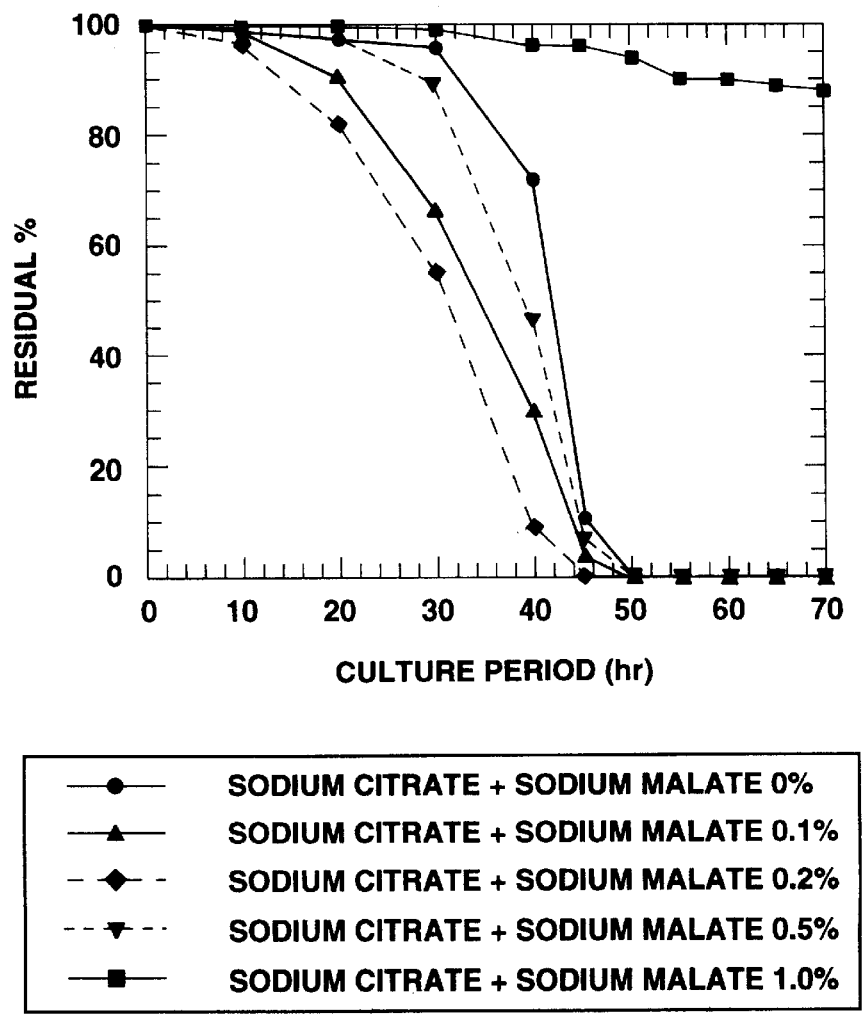
Figure 16:
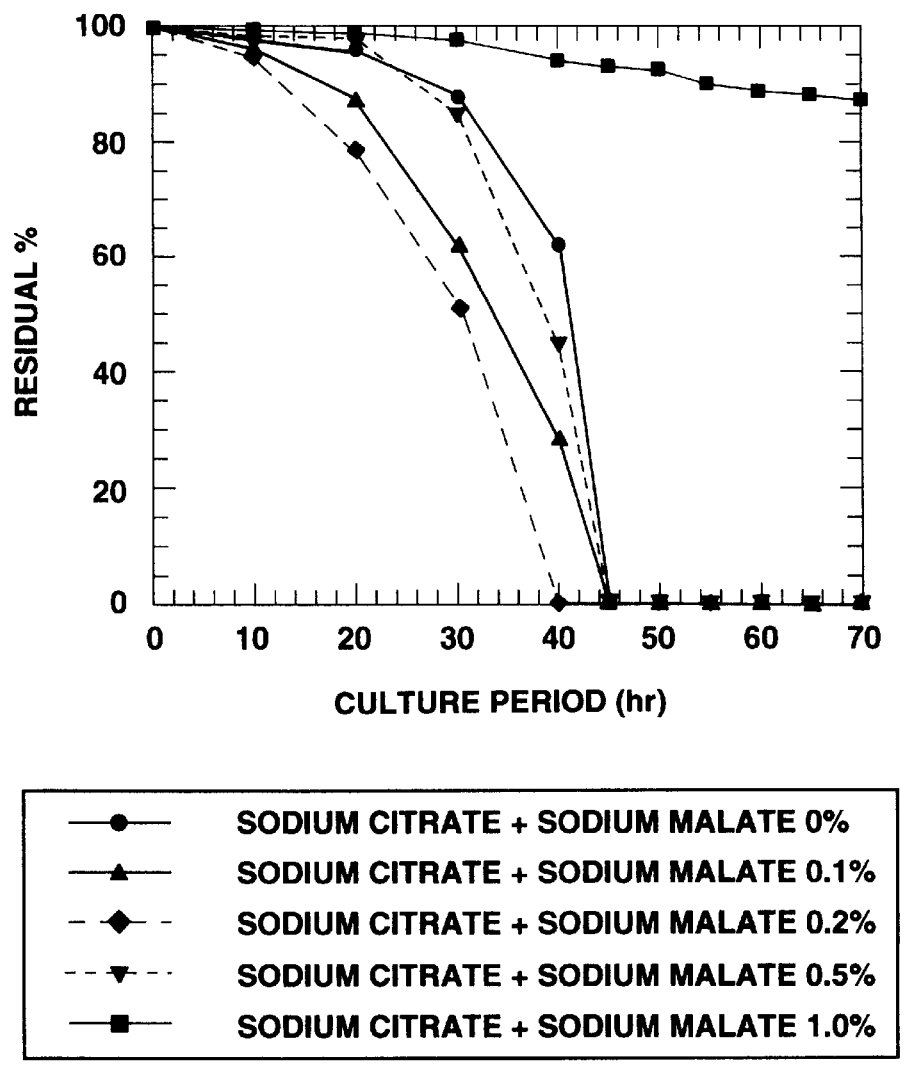

Degradation of TCE using strain JM1 (15° C., sand system) using various nutrients The procedure of Example 5 was repeated except that each sample of the M9 culture medium in each vial was cultured at 15° C. without shaking. The results are shown in FIGS. 14–16.

EXAMPLE 7

Figure 17:
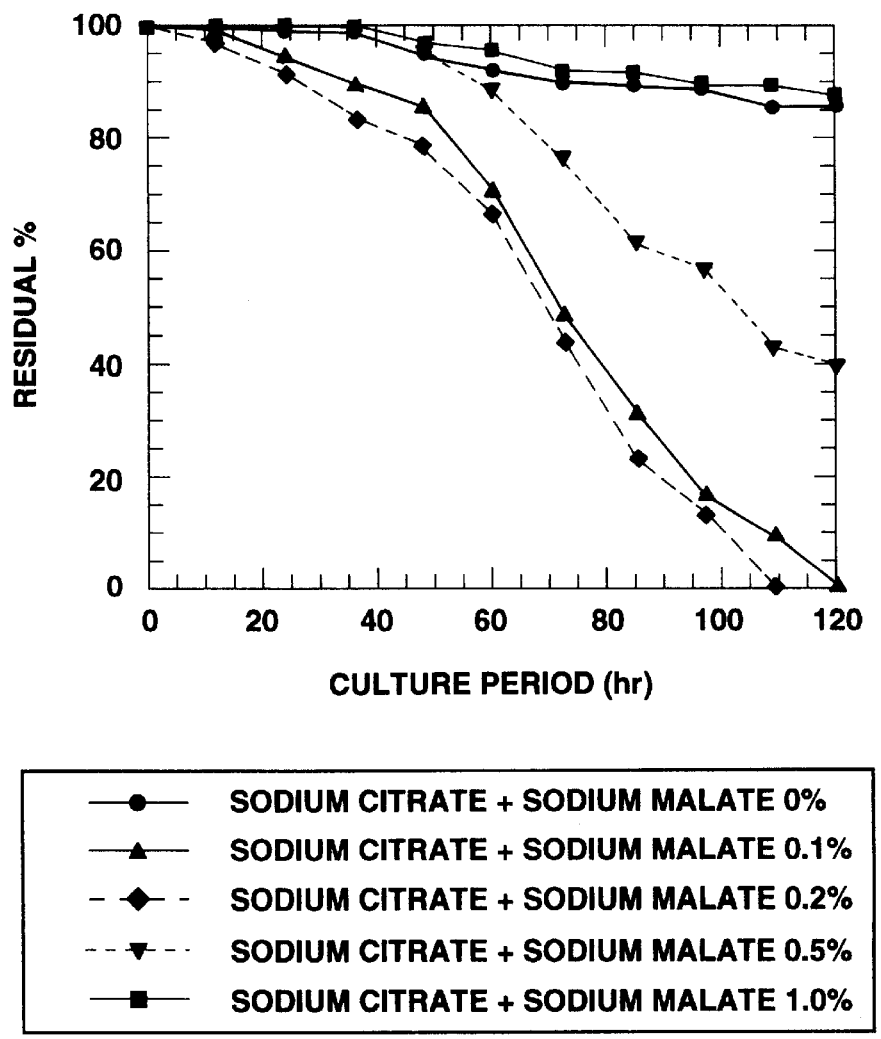
Figure 18:
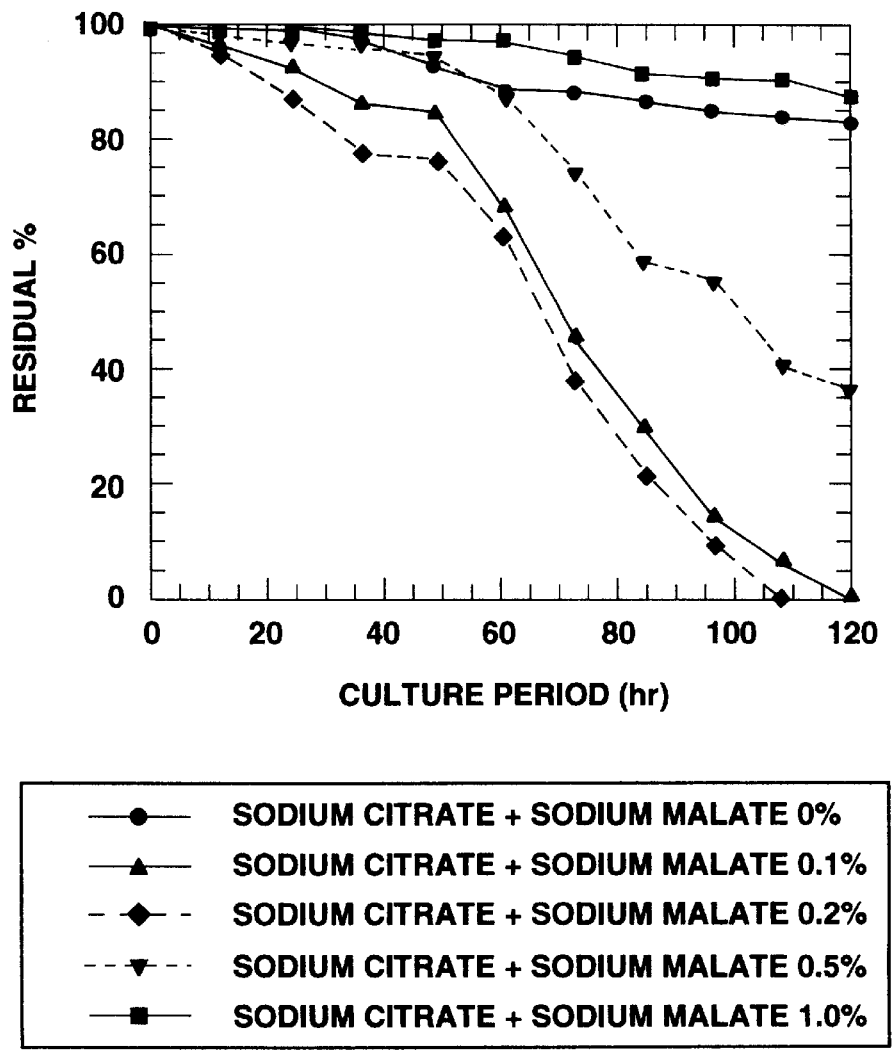
Figure 19:
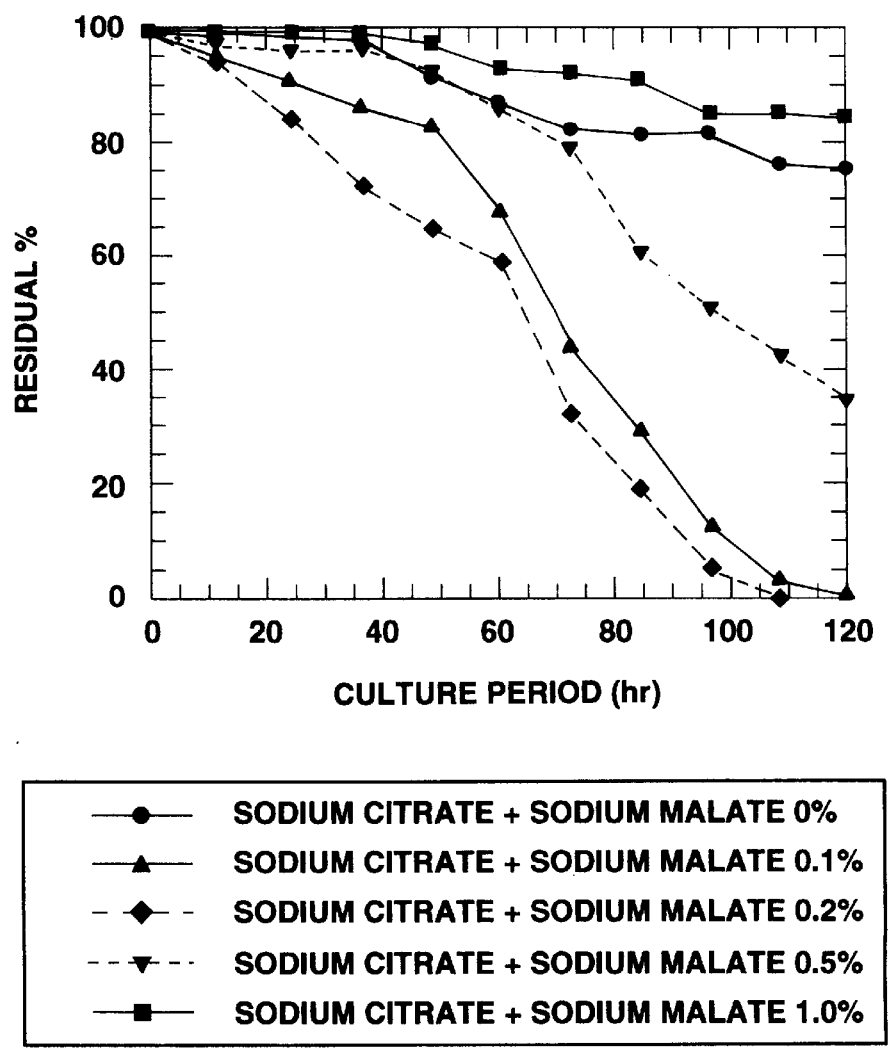

Degradation of TCE using strain JM1 (10° C., sand system) using various nutrients The procedure of Example 5 was repeated except that each vial was cultured without shaking at 10° C. The results are shown in FIGS. 17–19.

EXAMPLE 8

Figure 20:
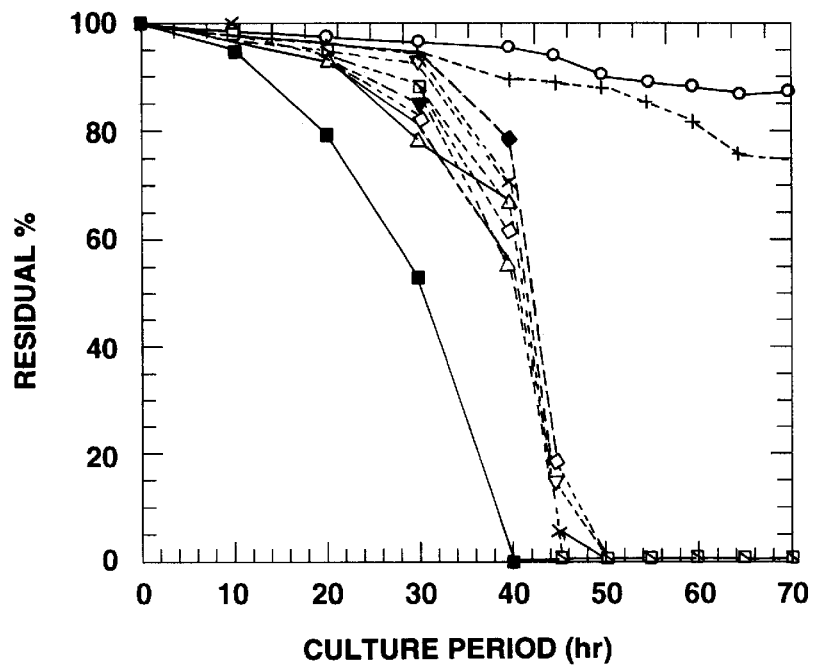
Figure 20:
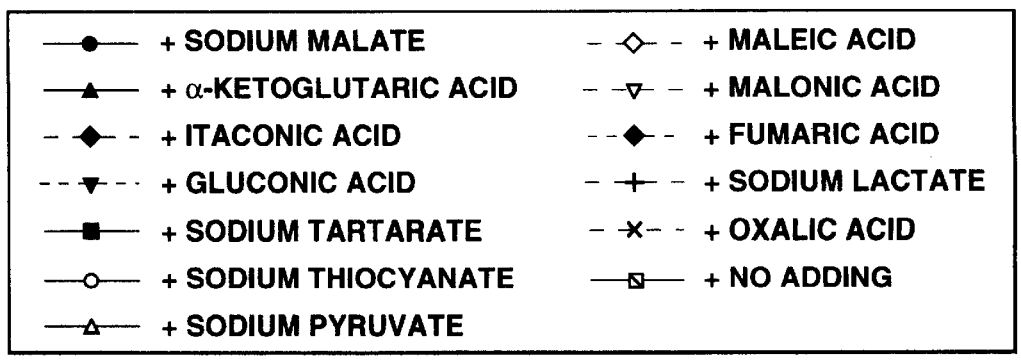

Degradation of TCE using strain JM1 (15° C., sand system) using various nutrients The strain JM1 was precultivated as described in Example 1. Once sample of M9 culture medium (6 ml) which included 2.0% of sodium citrate and 12 samples of M9 culture medium (6 ml) which included 2.0% concentration of various organic acids and organic salts. These were sodium malate, alpha-ketoglutaric acid, itaconic acid, gluconic acid, tartaric acid, sodium thiocyanate, sodium pyruvate, maleic acid, malonic acid, fumaric acid, sodium lactate and oxalic acid. Each sample of the M9 culture medium was inoculated with 60 μl (1/100 volume) of precultivated strain JM1. A plurality of 67.5 ml vials to which 60 grams of Sawara sand had been introduced was provided, and the above mentioned prepared samples of M9 culture medium were introduced into the vials. Each vial was closed by a butyl rubber stopper and an aluminium stopper. Air containing TCE was introduced into these vials to give a final concentration of TCE of 10 ppm, after which the M9 culture medium was cultured at 15° C. without shaking. The residual TCE was measured continuously by the headspace method using gas chromatography (FID detector). To provide a reference signal the quantity of TCE was measured in the same way for a similar system in which the strain JM1 was not present. The results obtained for the reference sample and for the samples of the invention are shown in FIG. 20.

EXAMPLE 9

Figure 21:
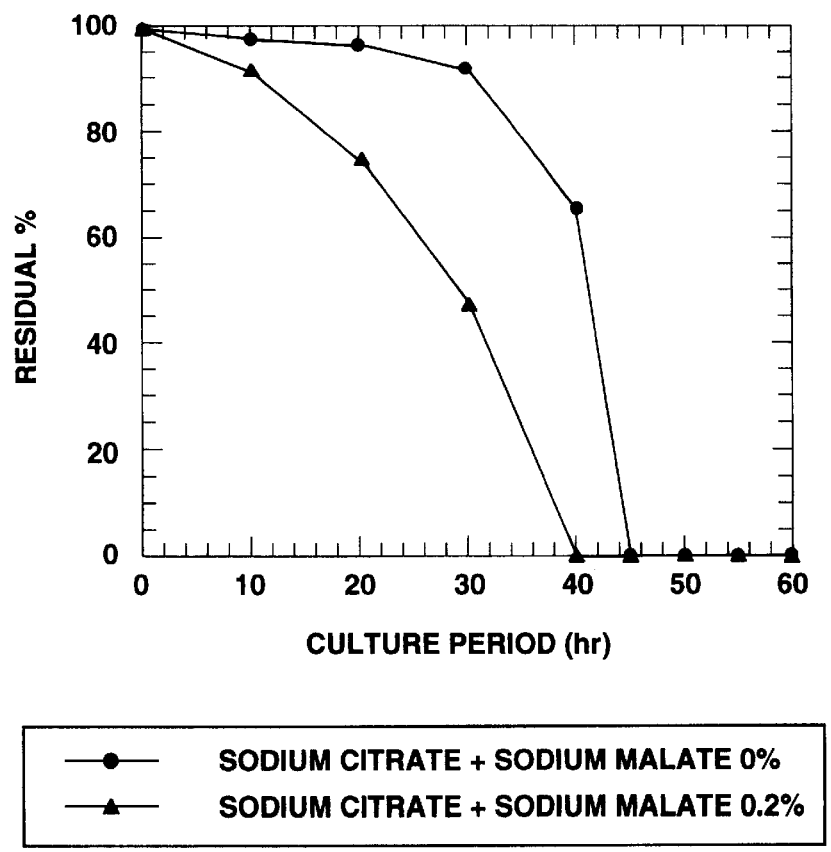
Figure 22:
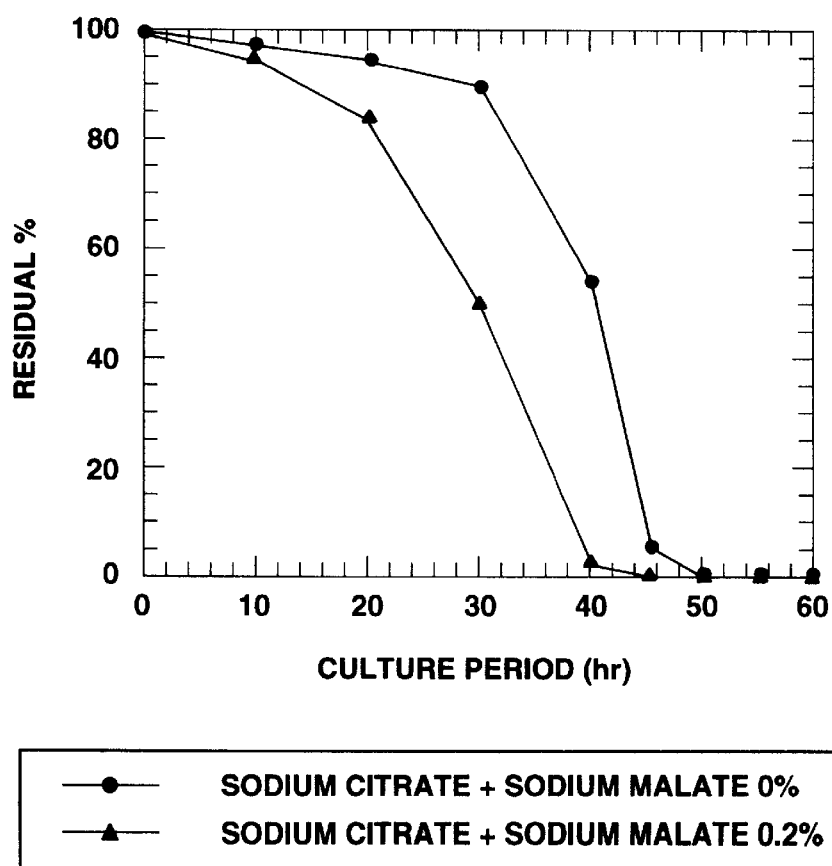
Figure 23:
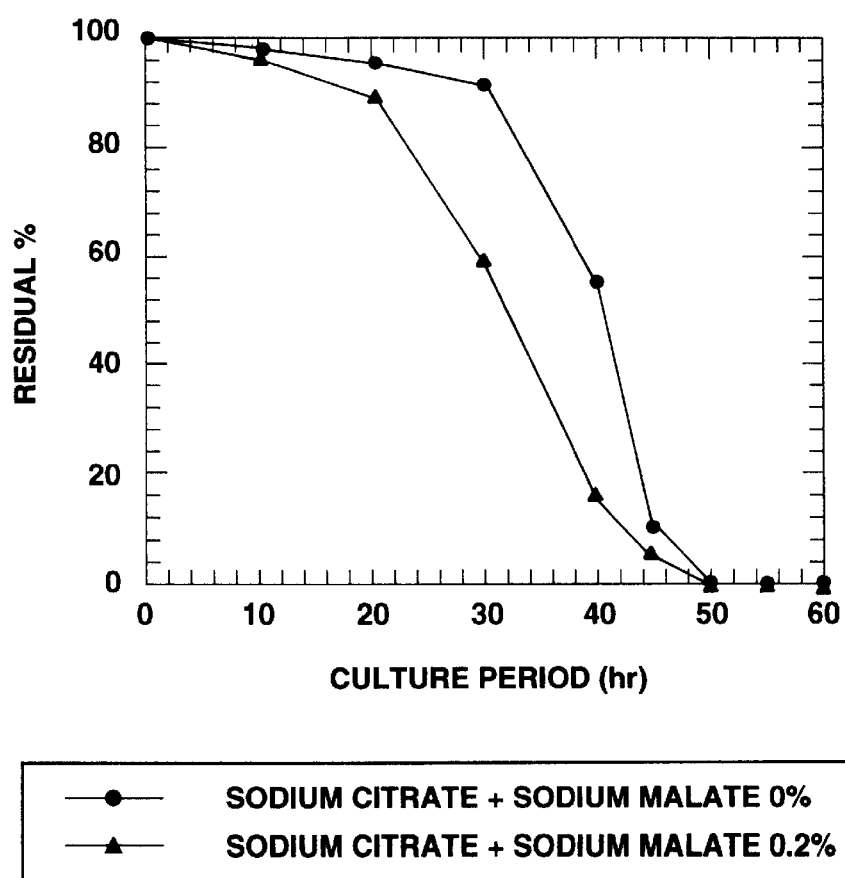

Degradation of DCE using strain JM1 (15° C., sand system) using various nutrients The strain JM1 was precultivated as in Example 1. A sample of M9 culture medium (6 ml) which included 2% of sodium citrate and 0.2% of sodium malate was prepared, and this sample of M9 culture medium was inoculated with 60 μl (1/100 volume) of precultivated strain JM1. A number of 67.5 ml vials containing 60 grams of Sarawa sand were prepared. The above prepared M9 culture medium was introduced into the vials, each of which was closed by a butyl rubber stopper and an aluminium stopper. Air including cis-1-2-dichloroethylene (cis-1,2-DCE) was introduced into the vials to give a final DCE concentration of 10 ppm. Then the M9 culture medium was grown at 15° C. without shaking and the capacity of the culture to degrade DCE was continuously measured. Residual TCE was monitored by the headspace method using gas chromatography (FID detector). The quantity of DCE in a reference sample which was similar except that the strain JM1 had not been added was also measured. Residual DCE was measured both for the reference sample and for the samples of the invention and the results are shown in FIG. 21. Further experiments which used trans-1,2-dichloroethylene (trans-1,2-DCE) and 1,1-dichloroethylene (1,1-DEC) instead of cis-1,2-dichloroethylene in the above mentioned Example were carried out and the results obtained are shown in FIGS. 22 and 23.

EXAMPLE 10

Figure 24:
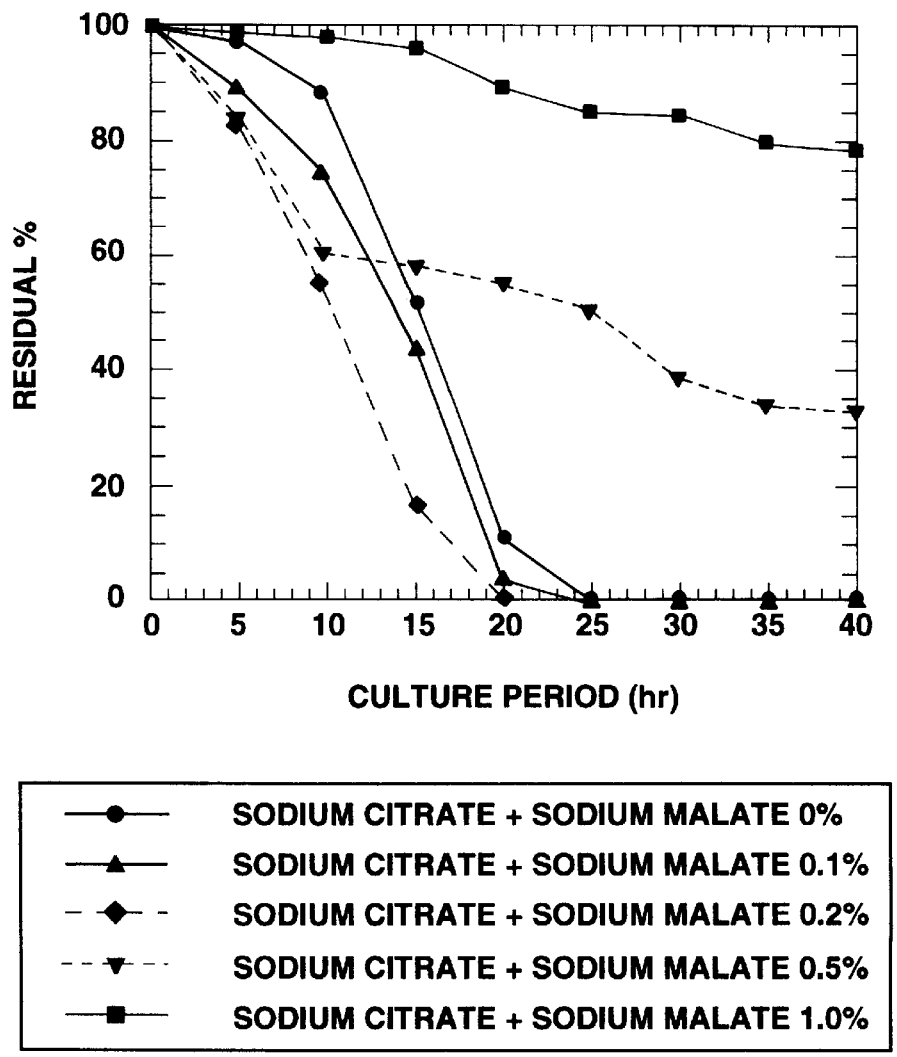

Degradation of TCE using strain JM1 (30° C., polluted water system) using various nutrients The strain JM1 was precultivated as described in Example 1. 20ml of water having a moderate level of pollution was obtained from a reservoir in Atsugi city, Kanagawa prefecture, Japan. Then 2ml of 10×M9 culture medium and minerals were added into the 20ml of polluted water to provide six samples of polluted water. Each sample was treated with sodium citrate to give a final concentration of sodium citrate of 2%, and sodium malate was added to give a final concentration of sodium malate respectively 0, 0.1, 0.2, 0.5, 1 and 2%. Then each sample of the polluted water with the source of conjugated carbon present was inoculated with 60 μl (1/100 volume) of precultivated strain JM1. Each polluted water sample was closed by a butyl rubber stopper and an aluminium stopper. Air including TCE was introduced into the samples to give a final TCE concentration of 10 ppm. Then the culture medium was grown at 30° C. with vibration. The TCE degradation power of the culture was measured continuously. The quantity of residual TCE was measured by the headspace method using gas chromatography (FID detector). To provide a reference sample the quantity of TCE was measured in the same way for a system in which the strain JM1 had not been added. The results for the reference sample and for the samples according to the invention are shown in FIG. 24.

EXAMPLE 11

Figure 25:
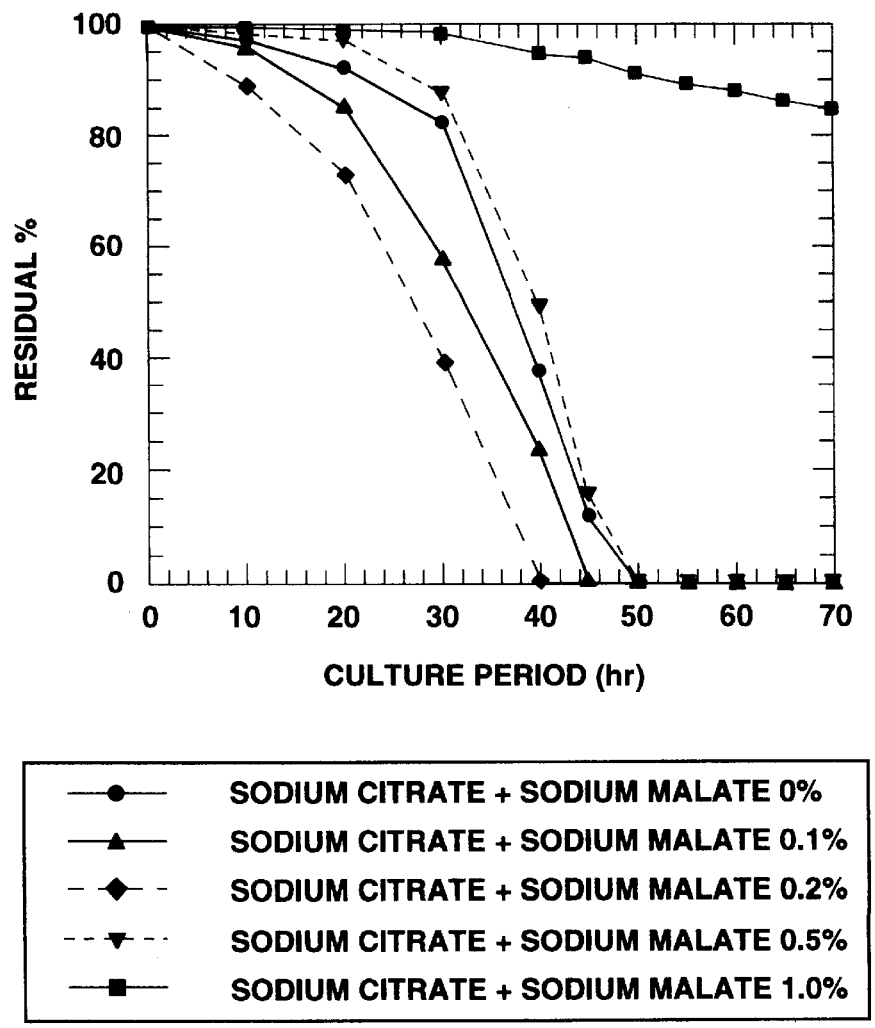

Degradation of TCE using strain JM1 (15° C., polluted water system) using various nutrients The decrease in TCE was measured in the same way as in Example 10 except that the cultivation temperature was 15° C. The results are shown in FIG. 25.

EXAMPLE 12

Figure 26:
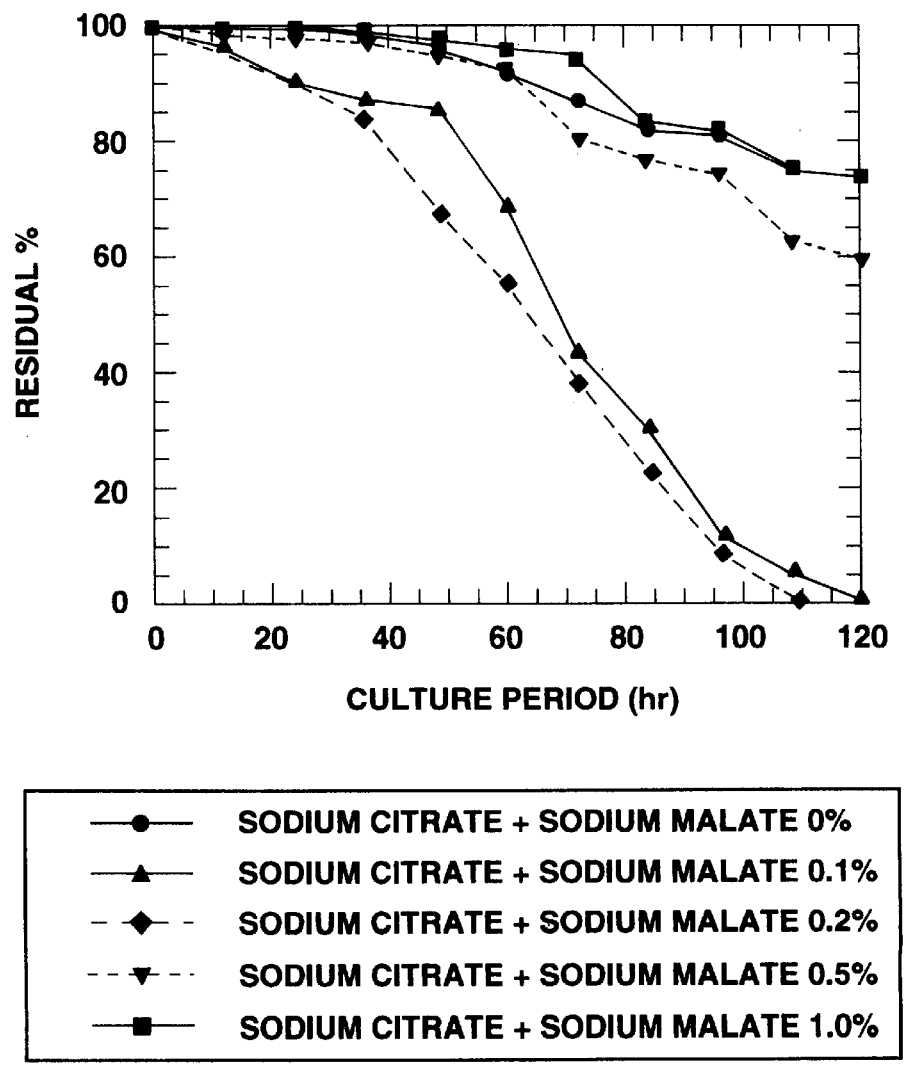

Degradation of TCE using strain JM1 (10° C., polluted water system) using various nutrients The decrease in TCE was measured in the same way as in Example 10 except that the cultivation temperature was 10° C. The results are shown in FIG. 26.

EXAMPLE 13

Figure 27:
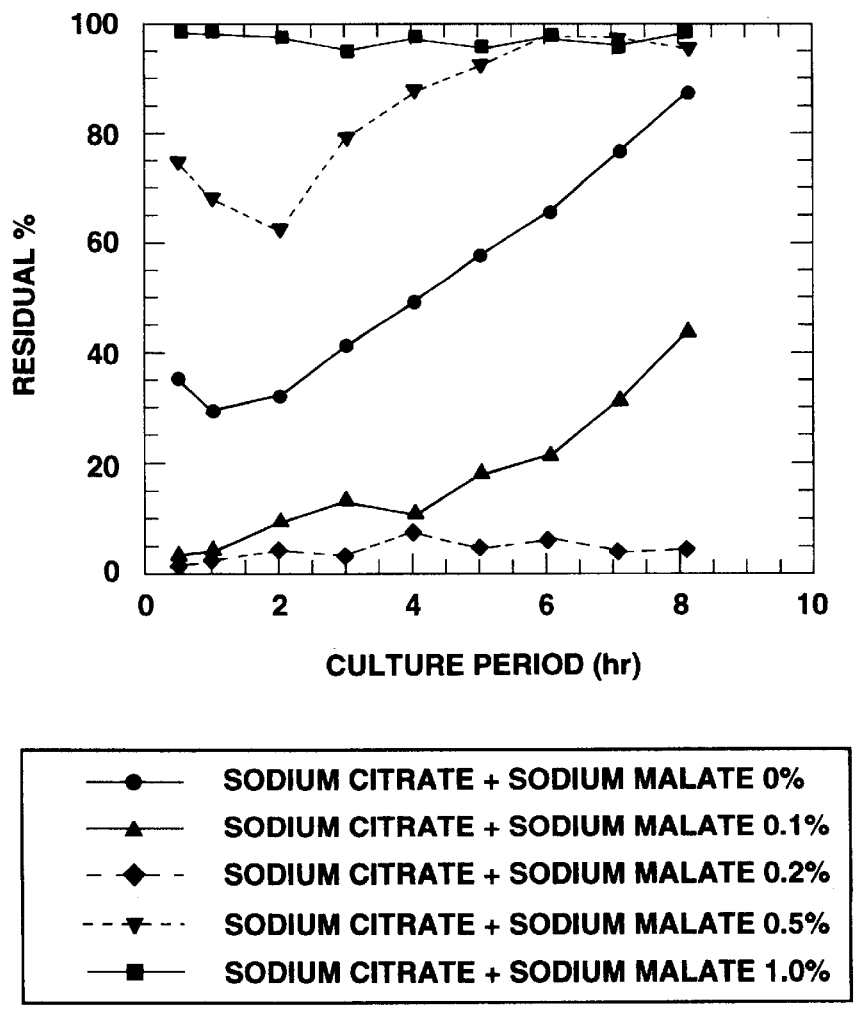

Degradation of TCE using strain JM1 (30° C., soil, continuous gas permeability system) using various nutrients The strain JM1 was precultivated as disclosed in Example 1 after which six samples of M9 culture medium (6 ml) including 0.5% of sodium citrate and respectively 0%, 0.1%, 0.2%, 0.5%, 1% and 2% of sodium malate were prepared. Each example of the M9 culture medium was inoculated with 60 μl (1/100 volume) of precultivated strain JM1. Then medium brown forest soil was added to each of the M9 culture media up to the level of the liquid surface. Each sample was closed by a silicone stopper and cultured at 30° C. for 24 hours after which excess cultivation liquid was removed as a decant. Each sample was then closed by a butyl rubber stopper and an aluminium stopper. Air which had been exposed to 100 ppm concentration TCE liquid was flowed into the soil at a rate of 1.5 ml/minute and cultivation was carried out without shaking at a temperature of 30° C. The quantity of TCE present was continuously measured by measuring the TCE quantity in the current of air using gas chromatography. The results are shown in FIG. 27.

EXAMPLE 14

Figure 28:
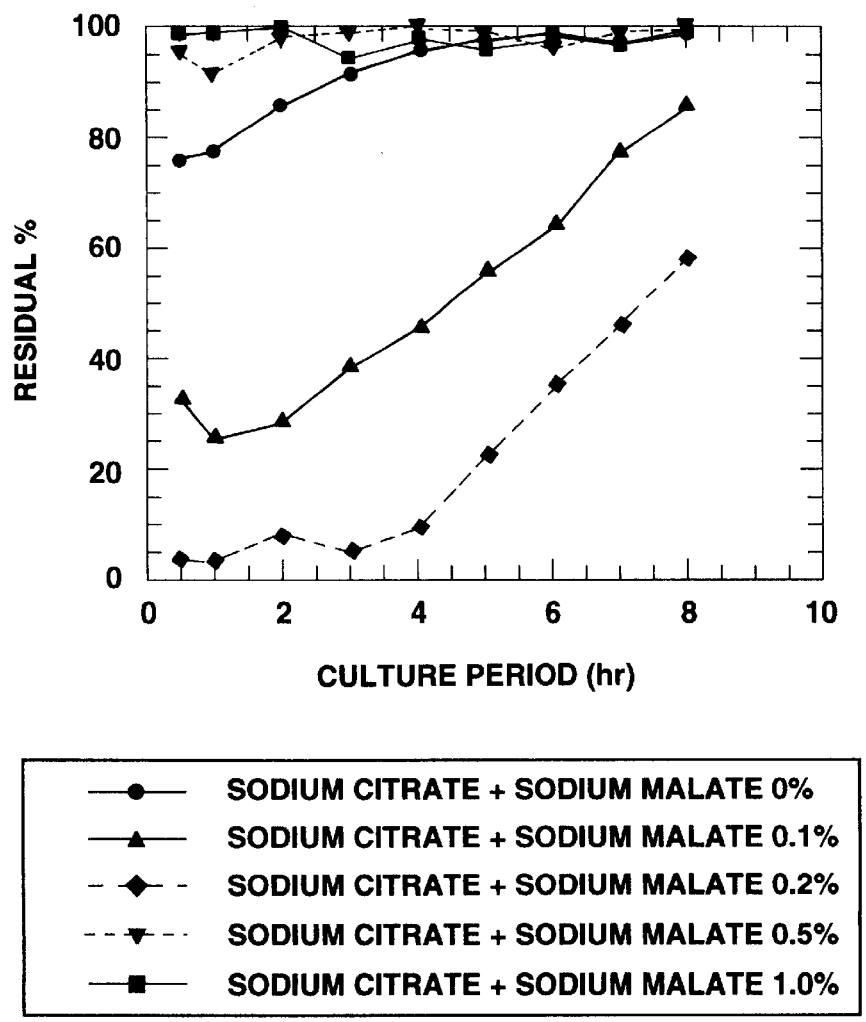

Degradation of TCE using strain JM1 (15° C., soil continuous gas permeability system) using various nutrients The procedure of Example 13 was repeated except that after the brown forest soil had been added, cultivation was carried out at 15° C. for 48 hours and the temperature during introduction of TCE was controlled to be 15° C. The results are shown in FIG. 28.

EXAMPLE 15

Figure 29:
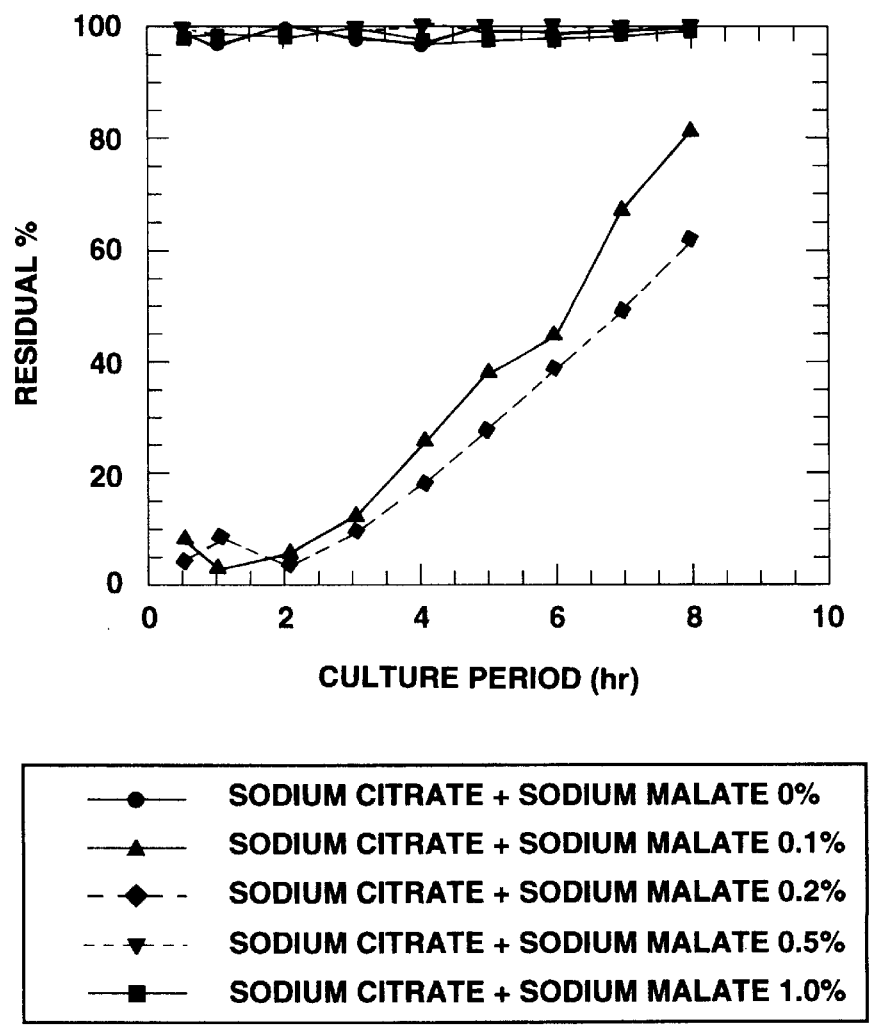

Degradation of TCE using strain JM1 (10° C., soil continuous gas permeability system) using various nutrients The decrease in TCE was measured as in Example 13 except that after the brown forest soil had been added, cultivation was carried out at 10° C. for 72 hours and the cultivation temperature during the introduction of TCE was maintained at 10° C. The results are shown in FIG. 29.

We claim:

1. A process for the biodegradation of an organic compound using JM1 (FERM BP5352), which process comprises the steps of:

contacting the JM1 with the organic compound; and culturing the JM1 in a medium which includes a source of conjugated carbon which comprises citric acid or a salt thereof and malic acid or a salt thereof.

2. The process of claim 1, wherein the concentration of the citric acid or salt in the culture medium is 0.5–2%.

3. The process of claim 1, wherein the concentration of the malic acid or salt in the culture medium is 0.1–1%.

4. The process of claim 1, wherein the JM1 is precultivated using an organic acid.

5. The process of claim 4, wherein the organic acid is malic acid or a salt thereof.

6. The process of claim 1, wherein the organic compound is a chlorinated aliphatic hydrocarbon.

7. The process of claim 6, wherein the chlorinated aliphatic hydrocarbon is trichloroethylene or dichloroethylene.

8. The process of claim 1, wherein the organic compound is an aromatic compound.

9. The process of claim 8, wherein the aromatic compound is phenol, toluene or cresol.

10. The process of claim 1, wherein the cultivation of the JM1 in the culture medium is carried out at the same time as the degradation of the organic compound by the JM1.

11. The process of claim 1, when used to upgrade an environment by reducing organic compounds which are pollutants present therein.

12. The process of claim 11, wherein the environment is a liquid environment.

13. The process of claim 12, wherein the degradation of the pollutant is carried out by contacting with the liquid a carrier carrying the JM1 organism.

14. A process according to claim 13, wherein the liquid is introduced into one part of a vessel containing the carrier carrying the JM1, and the liquid is discharged from a different part of the vessel.

15. The process of claim 11, wherein the environment is soil.

16. The process of claim 15, further comprising introducing an aqueous medium which includes JM1 into the soil and introducing the source of conjugated carbon into the soil.

17. The process of claim 16, wherein oxygen is introduced into the soil.

18. The process of claim 15, wherein the JM1 organism is introduced under pressure into the soil from an introduction port provided in the soil.

19. A process according to claim 15, wherein the soil is introduced into a liquid phase containing JM1.

20. A process according to claim 19, wherein a carrier carrying the JM1 organism contacts with the soil.

21. A process according to claim 11, wherein the environment is air.

22. The process of claim 21, wherein the air is introduced into liquid containing the JM1 organism.

23. The process of claim 21, wherein a carrier carrying the JM1 is in contact with the air.

24. The process of claim 21, wherein air is introduced into one part of a vessel containing a carrier carrying the JM1 organism, and air is discharged from another part of the vessel.

25. A process according to claim 24, wherein the pollutant is an aromatic compound.

26. The process of claim 25, wherein the aromatic compound is selected from phenol, toluene or cresol.

27. A process according to claim 11, wherein the pollutant is a chlorinated aliphatic hydrocarbon.

28. The process of claim 27, wherein the chlorinated aliphatic hydrocarbon is dichloroethylene or trichloroethylene.

29. The process of claim 11, wherein the JM1 and the pollutant are contacted at the same time as the JM1 organism is cultured.

* * * * *

UNITED STATES PATENT AND TRADEMARK OFFICE
CERTIFICATE OF CORRECTION

PATENT NO. : 5,854,059

DATED : December 29, 1998

INVENTOR(S) : SHINYA KOZAKI ET AL.    Page 1 of 3

It is certified that error appears in the above-identified patent and that said Letters Patent is hereby corrected as shown below:

On the title page, item
[56] REFERENCES CITED

Other Publications
"Preprint Preprint" should read --Preprint--.
"Growth of Microalgae...and No$_x$. 28/29" should read
    --"Growth of Microalgae...and No$_x$. 28/29"--.
"Trichloroethylene Degradation...JMP134," should read
    --"Trichloroethylene Degradation...JMP134,"--.

[57] ABSTRACT

Line 3, "source" should read --a source--.

COLUMN 2

Line 13, "1951 (1989)," should read --951 (1988),--.
Line 16, "Psudo-" should read --Pseudo- --.
Line 26, Close up left margin.
Line 27, "(1990) ), Lactobacillus" should read
    --1990)), ¶ Lactobacillus--.
Line 44, "Nelson et al." should read --Nelson, et al.,--.

UNITED STATES PATENT AND TRADEMARK OFFICE
CERTIFICATE OF CORRECTION

PATENT NO.  : 5,854,059

DATED       : December 29, 1998

INVENTOR(S) : SHINYA KOZAKI ET AL.

It is certified that error appears in the above-identified patent and that said Letters Patent is hereby corrected as shown below:

COLUMN 2

Line 63, "like" should read --like,--.

COLUMN 3

Line 17, "Seales et al." should read --Seales, et al.,--.

COLUMN 7

Line 13, "concentration etc" should read
      --concentration, etc.--.
   Line 26, "optimise" should read --optimize--.
   Line 49, "can be used" should be deleted.
   Line 55, "materials can be used" should read
      --materials,--.

COLUMN 8

Line 57, "concentration" should read --concentration,--.
   Line 67, "dust" should read --duct--.

UNITED STATES PATENT AND TRADEMARK OFFICE
CERTIFICATE OF CORRECTION

PATENT NO. : 5,854,059

DATED : December 29, 1998

INVENTOR(S) : SHINYA KOZAKI ET AL.

It is certified that error appears in the above-identified patent and that said Letters Patent is hereby corrected as shown below:

COLUMN 9

```
Line 51, "15°C.," should read --(15°C.,--.
Line 52, "system" should read --system)--.
Line 58, "10°C.," should read --(10°C.,--; and
    "system" should read --system)--.
```

COLUMN 10

```
Line 38, "these." should read --these--.
```

Signed and Sealed this

Twenty-first Day of September, 1999

Attest:

Q. TODD DICKINSON

*Attesting Officer*      Acting Commissioner of Patents and Trademarks